(12) United States Patent
Anderson et al.

(10) Patent No.: US 10,324,000 B2
(45) Date of Patent: Jun. 18, 2019

(54) TEST FIXTURE FOR TENSIONING AND COOLING AN ARTICLE

(71) Applicant: The Boeing Company, Chicago, IL (US)

(72) Inventors: David Mitchell Anderson, Sammamish, WA (US); Aydin Akdeniz, Langley, WA (US); Blake A. Bertrand, Port Orchard, WA (US); Perry Thomas Horst, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 124 days.

(21) Appl. No.: 15/386,860

(22) Filed: Dec. 21, 2016

(65) Prior Publication Data

US 2018/0172549 A1 Jun. 21, 2018

(51) Int. Cl.
*G01M 7/02* (2006.01)
*G01N 1/42* (2006.01)
(Continued)

(52) U.S. Cl.
CPC .............. *G01M 7/027* (2013.01); *G01N 1/42* (2013.01); *G01N 3/04* (2013.01); *G01N 3/08* (2013.01);
(Continued)

(58) Field of Classification Search
CPC ...... G01M 7/027; G01N 1/42; G01N 2203/17
(Continued)

(56) References Cited

U.S. PATENT DOCUMENTS 3,563,086 A 2/1971 Flood, Jr.
3,795,134 A 3/1974 Eichenbrenner et al.
(Continued)

FOREIGN PATENT DOCUMENTS

GB 1308378 A 2/1973
JP 2010286479 A * 12/2010

OTHER PUBLICATIONS

Advisory Circular; "Powerplant Installation and Propulsion System Component Fire Protection Test Methods, Standards, and Criteria"; US Department of Transportation, Federal Aviation Administration; AC No. 20-135; pp. 1-13 (Feb. 6, 1990).
(Continued)

*Primary Examiner* — Natalie Huls
*Assistant Examiner* — Monica S Young
(74) *Attorney, Agent, or Firm* — Vivacqua Law

(57) ABSTRACT

A test fixture for securing a test article is disclosed. The test fixture comprises a frame, an upper grip, a lower grip, a tensioner assembly, and a cooling assembly. The frame defines an upper portion and a lower portion, where the lower portion of the frame is configured to be releasably mounted to a vibration device. The upper grip is connected to the upper portion of the frame and the lower grip is connected to the lower portion of the frame. The upper grip is configured to secure an upper portion of the test article along an upper interface, and the lower grip is configured to secure a lower portion of the test article along a lower interface. The tensioner assembly is located at the upper portion of the test fixture. The cooling assembly transports a cooling medium across at least one of the upper interface and the lower interface.

20 Claims, 19 Drawing Sheets

(51) Int. Cl.
*G01N 3/04* (2006.01)
*G01N 3/08* (2006.01)
*G01N 3/32* (2006.01)

(52) U.S. Cl.
CPC ....... *G01N 3/32* (2013.01); *G01N 2203/0005* (2013.01); *G01N 2203/0222* (2013.01); *G01N 2203/0226* (2013.01); *G01N 2203/0228* (2013.01)

(58) Field of Classification Search
USPC ............................................................ 73/83
See application file for complete search history.

(56) References Cited

U.S. PATENT DOCUMENTS

| | | | | |
|---|---|---|---|---|
| 4,912,980 | A * | 4/1990 | Baughn | G01M 7/027 73/663 |
| 5,945,607 | A * | 8/1999 | Peppel | G01N 3/04 73/831 |
| 2002/0017144 | A1 * | 2/2002 | Miles | G01N 3/32 73/808 |
| 2014/0123773 | A1 * | 5/2014 | Lemmer | G01K 13/12 73/863.01 |
| 2015/0020603 | A1 | 1/2015 | Kismarton et al. | |
| 2015/0160108 | A1 | 6/2015 | Kimura | |
| 2015/0233709 | A1 | 8/2015 | Griess et al. | |
| 2015/0355057 | A1 * | 12/2015 | Saari | G01N 3/18 73/863.02 |
| 2017/0016952 | A1 * | 1/2017 | Serafim | G01R 31/2817 |
| 2018/0209110 | A1 * | 7/2018 | Lakin | E01H 5/00 |

OTHER PUBLICATIONS

Levine, Sheldon, "Vibration test fixtures: theory and practice"; Aero Nav Laboratories; pp. 1-2 (at least as early as Jul. 23, 2008).
EP, Search Report; EP Patent Application 17191381.7, 10 pages (dated Mar. 23, 2018).

* cited by examiner

TEST FIXTURE FOR TENSIONING AND COOLING AN ARTICLE

FIELD

The disclosed system and method relate to a test fixture releasably mounted to a vibration device, more particularly, to a test fixture for exerting a tension load upon a test article, where the test fixture includes one or more features that provide cooling.

BACKGROUND

Aviation regulations may require that test panels and other related structures comply with specific requirements. For example, some requirements are presently interpreted to include exerting load and vibration upon the component during a test, while subjecting the component to heat at the same time. Test fixtures may be used to mount the panel to a vibration device, such as a vibration table, in order to undergo testing. The test fixture is expected to be capable of exerting tension upon the panel. Limitations in the force, stiffness, and weight of the vibration device are generally considered when selecting a test fixture as well. This is because some vibration devices may not be able to accommodate relatively heavy or bulky test fixtures. Thus, it may be desirable to utilize the lightest, most compact test fixture presently available. However, known test fixtures are only able to satisfy two of the three testing conditions (e.g., vibration and heat, but not tension).

SUMMARY

In one example, a test fixture for securing a test article is disclosed. The test fixture comprises a frame, an upper grip, a lower grip, a tensioner assembly, and a cooling assembly. The frame defines an upper portion and a lower portion, where the lower portion of the frame is configured to be releasably mounted to a vibration device. The upper grip is connected to the upper portion of the frame and the lower grip is connected to the lower portion of the frame. The upper grip is configured to secure an upper portion of the test article at an upper interface, and the lower grip is configured to secure a lower portion of the test article at a lower interface. The upper interface and the lower interface both define a boundary where the test article and either the upper grip or the lower grip engage with one another. The tensioner assembly is located at the upper portion of the test fixture. The tensioner assembly is connected to the upper grip and includes an adjustment mechanism configured to urge the upper grip in an upward direction towards the upper portion of the frame. The cooling assembly transports a cooling medium across at least one of the upper interface and the lower interface.

In another example, a system for testing a test article is disclosed. The system includes a vibration device defining a surface, and a test fixture. The test fixture comprises a frame, an upper grip, a lower grip, a tensioner assembly, and a cooling assembly. The frame defines an upper portion and a lower portion, where the lower portion of the frame is releasably mounted to the surface of the vibration device. The upper grip is connected to the upper portion of the frame and the lower grip is connected to the lower portion of the frame. The upper grip is configured to secure an upper portion of the test article at an upper interface, and the lower grip is configured to secure a lower portion of the test article at a lower interface. The upper interface and the lower interface both define a boundary where the test article and either the upper grip or the lower grip engage with one another. The tensioner assembly is located at the upper portion of the test fixture. The tensioner assembly is connected to the upper grip and includes an adjustment mechanism configured to urge the upper grip in an upward direction towards the upper portion of the frame. The cooling assembly transports a cooling medium across at least one of the upper interface and the lower interface.

In yet another example, a method of testing a panel is disclosed. The method comprises coupling a test fixture to a surface of a vibration device, where the test fixture includes a frame defining an upper portion and a lower portion. The test fixture is releasably mounted to the surface at the lower portion of the frame. The method further comprises securing an upper portion of the test article to an upper grip at an upper interface, and a lower portion of the test article to a lower grip at a lower interface, where the upper grip is connected to the upper portion of the frame and the lower grip is connected to the lower portion of the frame. The upper interface and the lower interface both define a boundary where the test article and either the upper grip or the lower grip engage with one another. The method further comprises urging the upper grip in an upward direction towards the upper portion of the test article by an adjustment mechanism of a tensioner assembly. The tensioner assembly is located at the upper portion of the test fixture and is connected to the upper grip. Finally, the method comprises transporting a cooling medium across at least one of the upper interface and the lower interface by a cooling assembly.

Other objects and advantages of the disclosed method and system will be apparent from the following description, the accompanying drawings and the appended claims.

DETAILED DESCRIPTION

The test fixture described herein incorporates cooling features and insulation features in addition to meeting the vibration and tension force conditions. Further, the herein-described test fixture is a relatively lightweight and compact test fixture that accommodates subjecting a test panel to tension, vibration, and heat simultaneously.

Figure 1:
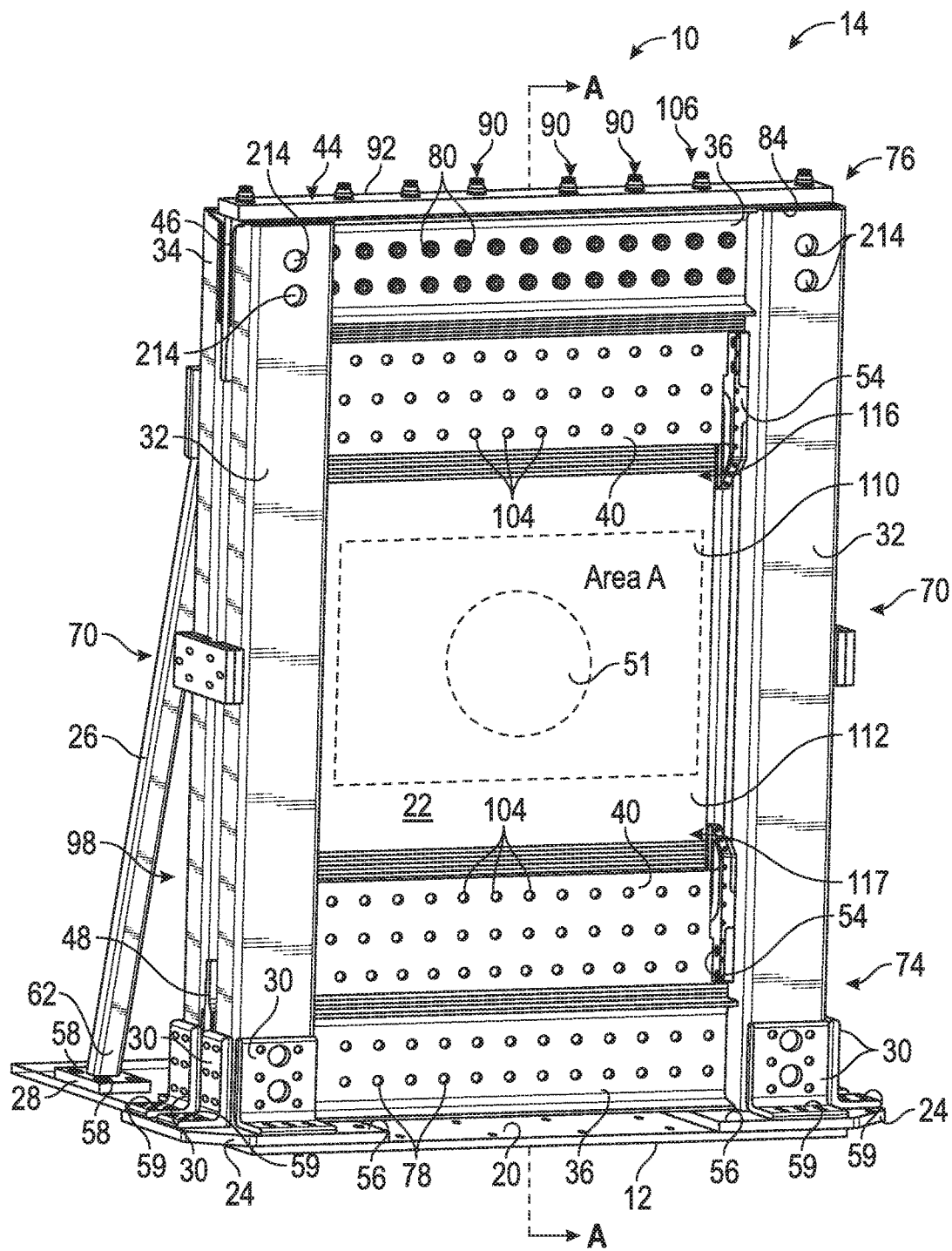
FIG. 1 is an exemplary illustration of the disclosed test fixture mounted upon a surface of a vibration device, where the test fixture is secures a test article, and where a pair of heat shields, insulation, and a portion of the fasteners of the test fixture are omitted.

FIG. 1 is an exemplary illustration of the disclosed test fixture 10 according to one embodiment of the disclosure. The test fixture 10 may be used with a vibration device 12. In the example as shown in FIG. 1, the test fixture 10 is releasably mounted to an upper surface 20 of the vibration device 12. Only the upper surface 20 of the vibration device 12 is illustrated in FIG. 1. The vibration device 12 may be any type of device that supports the weight of the test fixture 10 and a test article 22, and generates single-axis or multi-axis vibration such as, for example, a vibration table. The test fixture 10 is configured to secure the test article 22. A system 14 for testing the test article 22 includes the vibration device 12 and the test fixture 10.

Figure 2:
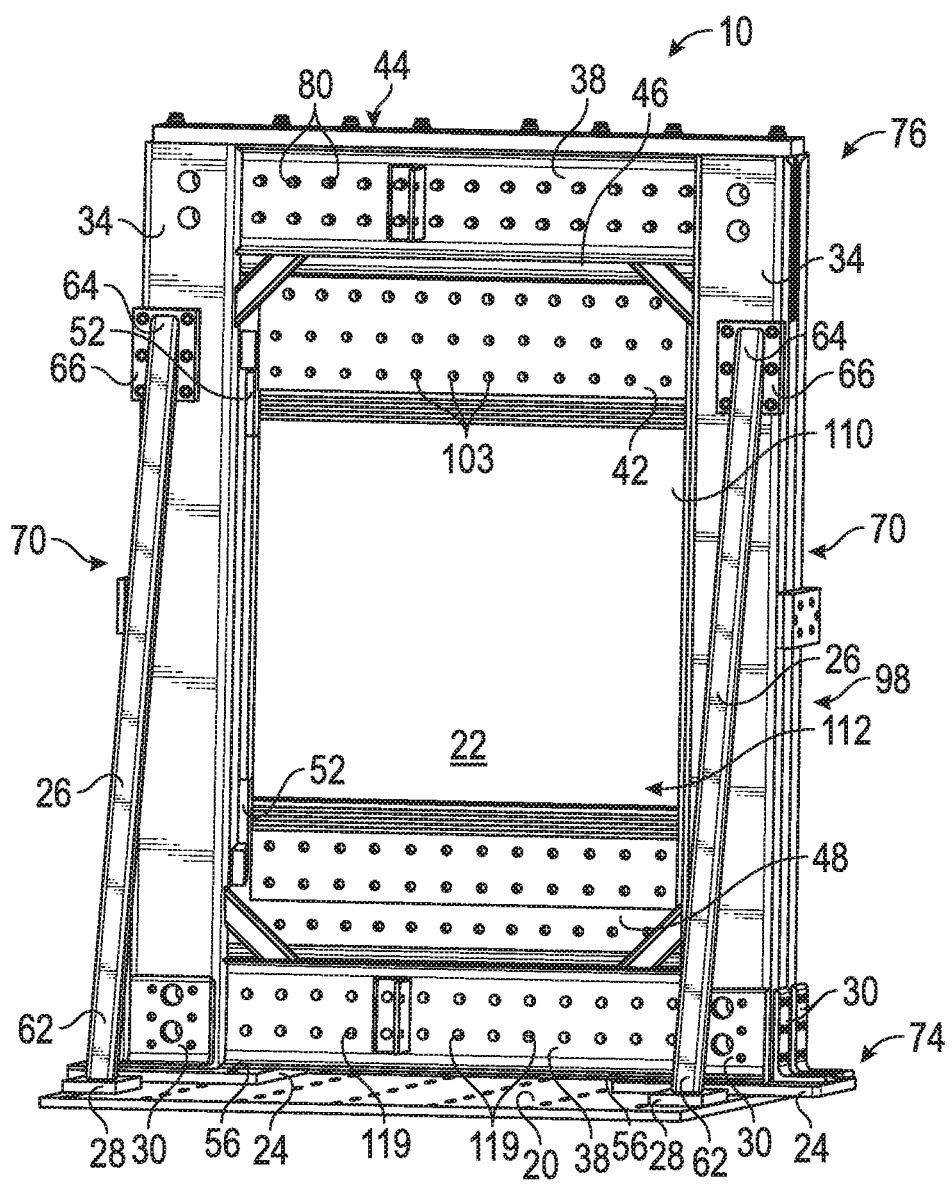
FIG. 2 is a rear perspective view of the test fixture shown in FIG. 1, where a lower rear grip plate is omitted.

In the exemplary embodiment as shown in both FIGS. 1 and 2, the test fixture 10 includes a front pair of footpads 24, a pair of rear side straps 26, a pair of rear footpads 28, a plurality of mounting brackets 30, a pair of vertically oriented front frame members 32, a pair of vertically oriented rear frame members 34, a pair of horizontally oriented front load frames 36, a pair of horizontally oriented rear load frames 38 (FIG. 2), a pair of front grip plates 40, a pair of rear grip plates 42 (seen in FIG. 4), a static tension plate 44, an upper adapter plate 46, a lower adapter plate 48, a pair of heat shields 50 (shown in FIGS. 13-16 and 19), two inlet manifolds 52 (visible in FIG. 2), and two outlet manifolds 54 (visible in FIG. 1). For purposes of simplicity and clarity, the heat shields 50 are not illustrated in FIGS. 1-7.

Referring back to FIG. 1, the test article 22 is any relatively flat component that is secured between the grip plates 40, 42 of the test fixture 10 to perform testing. The securement of the test article 22 by the grip plates 40, 42 is described in greater detail below. In one non-limiting embodiment, the test article 22 is a carbon fiber panel used in an aircraft. However, this embodiment is merely exemplary in nature, and a variety of other components may be utilized as the test article 22 as well such as, for example, components constructed of metallic based materials, glass fiber based material, organic based materials, or a combination of metallic, glass fiber, or organic based materials. Moreover, although FIG. 1 illustrates the test article 22 as an original, unmodified test panel, in another embodiment the panel may include a rework or repair patch as well (not illustrated).

Figure 19:
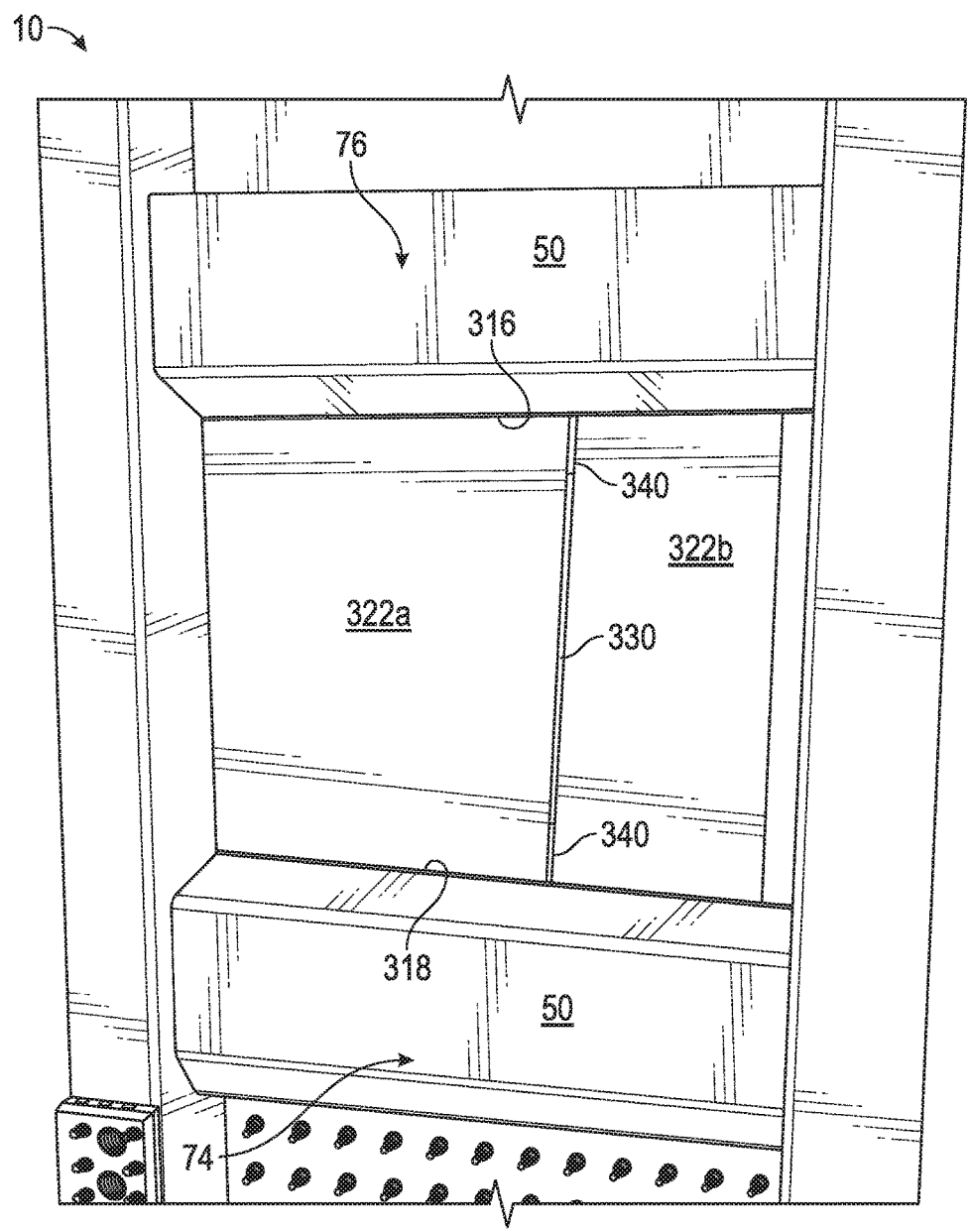
FIG. 19 is a front view of the test fixture securing a test article having two discrete sections.
Figure 20:
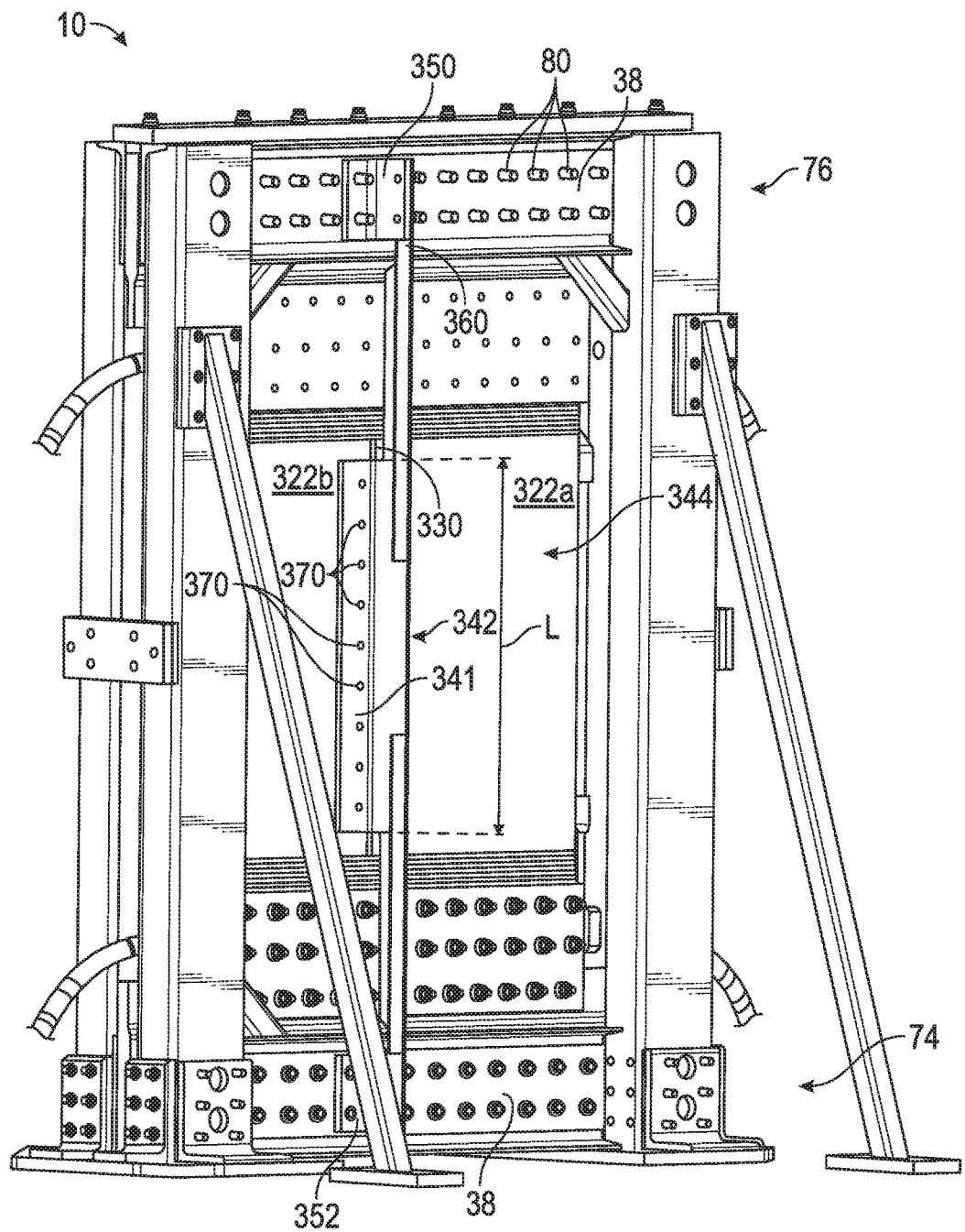
FIG. 20 is a rear perspective view of the two sections of the test article shown in FIG. 19, where a support member is attached to the test fixture.

As explained in greater detail below, the test article 22 is subjected to a tension load by the test fixture 10. In one embodiment, the test article 22 may be subjected to single or multi-axis vibrations generated by the vibration device 12, elevated temperatures, and the tension load simultaneously. In the embodiment as shown in FIGS. 1 and 2, the test article 22 is a single, unitary piece. However, this embodiment is non-limiting in nature, and the test article 22 may include a variety of configurations. For example, in one embodiment the test article 22 includes multiple discrete panels joined together, which is illustrated in FIGS. 19 and 20. The variety of configurations of the test article 22 is explained in greater detail below. Furthermore, although the test article 22 illustrated in FIG. 1 extends completely between the vertically oriented front frame members 32, this illustration is not limiting in nature. Indeed, in another approach the test article 22 may only extend partially between the two vertically oriented front frame members 32.

Figure 3:
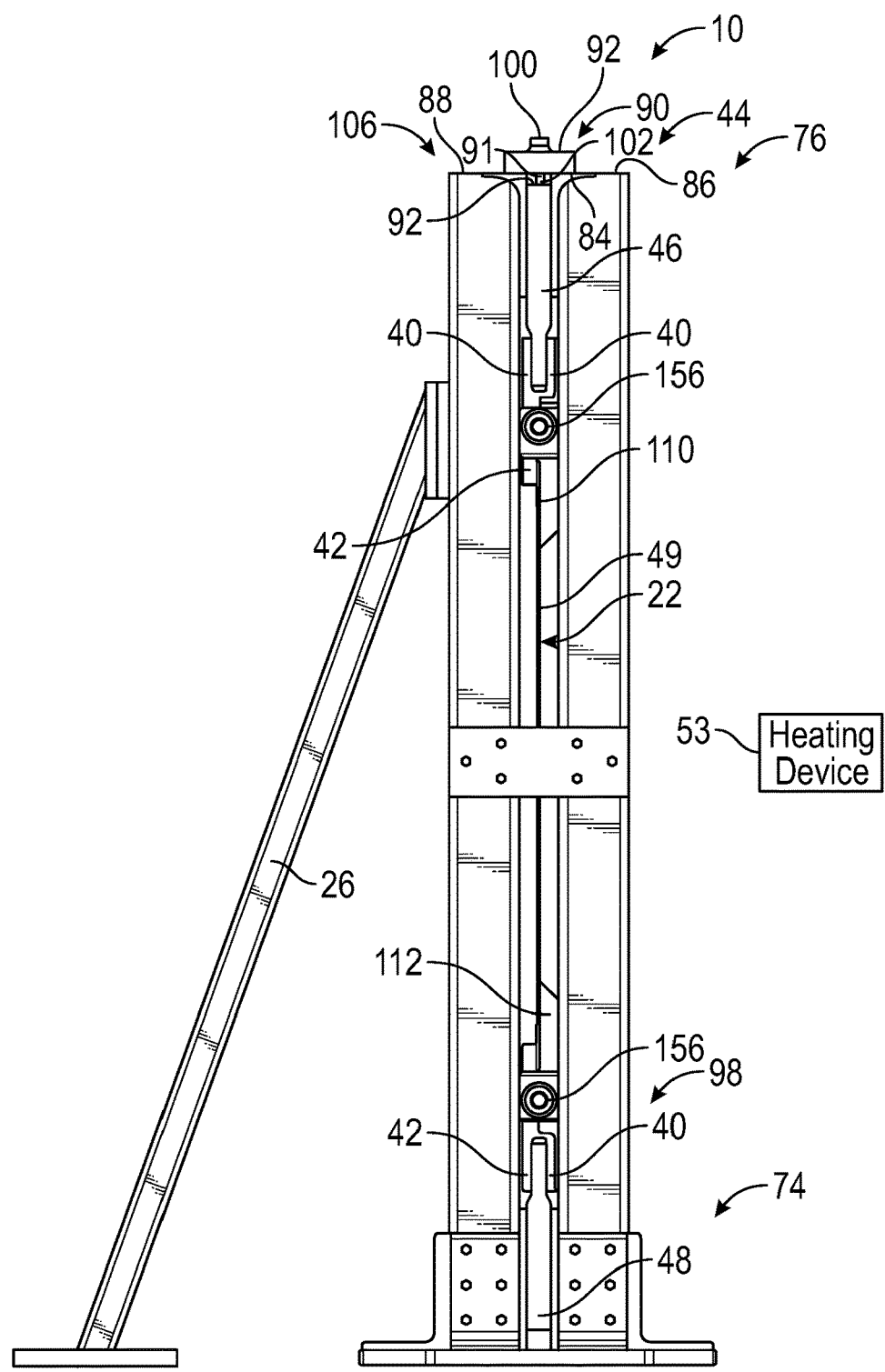
FIG. 3 is a side view of the test fixture shown in FIG. 1.

Turning now to FIG. 3, a front side 49 of the test article 22 faces a heating device 53. In the embodiment as illustrated, the heating device 53 may oppose a central area or portion 51 (seen in FIG. 1) of the test article 22. However, this embodiment is merely exemplary in nature and in another embodiment the heating device 53 may oppose any portion of the test article 22 within area A (seen in FIG. 1). Area A represents a central portion of the test article 22 which is not directly adjacent to one of the grip plates 40. The heating device 53 is positioned at a predetermined distance from the central portion 51 of the test article 22, and directs heat towards the test article 22. In one embodiment, the predetermined distance from the central portion 51 of the test article 22 is about 10.1 centimeters (4 inches), however this distance between the test article 22 and the heating device 53 is predetermined based on the test being performed. The heating device 53 may be any device for producing heat such as, for example, a burner producing a flame, an oven, or a quartz lamp.

The elevated temperatures produced by the heating device 53 may vary based on the specific test and the material of the test article 22. In one embodiment, the elevated temperature may be defined as any temperature equal to or greater than the minimum temperature required to reduce the load necessary to deform the material of the test article 22. For example, in one embodiment the heating device 53 may produce elevated temperatures of about 1093° C. (2000° F.) or more. However, this temperature is merely exemplary in nature and other temperatures may be produced depending upon the specific test performed.

Referring to both FIGS. 1 and 2, the front pair of footpads 24 and the rear footpads 28 may be releasably secured to the surface 20 of the vibration device 12 by any fastening approach such as, for example, fasteners. Although FIGS. 1 and 2 illustrate apertures 56 within the front pair of footpads 24 and apertures 58 in the rear footpads 28, the fasteners that may be received by the apertures 56, 58 are omitted from the figures. The mounting brackets 30 may also be releasably attached to the front pair of footpads 24 by any fastening approach as well. FIG. 1 illustrates apertures 59 within the mounting brackets 30 for receiving corresponding fasteners, however the fasteners are not illustrated.

The rear footpads 28 may each be attached to a first end 62 of one of the rear side straps 26. The rear side straps 26 may be positioned at an angle relative to the rear frame members 34. As seen in FIG. 2, a second end 64 of the rear side straps 26 may each be releasably attached to a corresponding end plate 66. Each end plate 66 may be releasably attached to one of the rear frame members 34. The rear side straps 26 may be provided in order to enhance the stability of the test fixture 10 when mounted upon the surface 20 of the vibration device 12.

Continuing to refer to both FIGS. 1 and 2, the front frame members 32 are each positioned at opposing sides 70 of the test fixture 10. Similarly, the rear frame members 34 are positioned at the opposing sides 70 of the test fixture 10. The front frame members 32 and the rear frame members 34 are constructed of a material that is capable of withstanding the elevated temperatures produced by the heating device 53 (FIG. 3). For example, in one embodiment the front frame members 32 and the rear frame members 34 are constructed of steel and include generally rectangular cross-sections. In another non-limiting embodiment, the front frame members 32 and the rear frame members 34 may include a generally C-shaped cross-section (i.e., a cross-sectional shape that is at least partially arcuate with a straight portion defined between ends of the arcuate portions).

Referring to FIG. 1, one of the front load frames 36 is disposed along a lower portion 74 of the test fixture, and a remaining one of the front load frames 36 is disposed along an upper portion 76 of the test fixture 10. Both of the front load frames 36 include a series of apertures 78 each shaped to receive a corresponding fastener 80. FIG. 1 illustrates the front load frame 36 disposed along the upper portion 76 with fasteners 80, but the current views illustrate the fasteners 80 omitted from the front load frame 36 disposed along the lower portion 74 of the test fixture 10. Therefore, the apertures 78 of the front load frame 36 disposed along the lower portion 74 are visible.

Referring now to FIG. 2, one of the rear load frames 38 is disposed along the lower portion 74 of the test fixture 10, and a remaining one of the rear load frames 38 is disposed along the upper portion 76 of the test fixture 10. The lower grip plate 42 has been omitted in FIG. 2 for clarity. Both of the rear load frames 38 also include a series of apertures 119 which are each shaped to receive the fasteners 80 shown in FIG. 1 (i.e., the fasteners 80 received by the front load frames 36). Similar to FIG. 1, the rear load frame 38 disposed along the upper portion 76 is installed with fasteners 80, while fasteners are omitted in the rear load frame 38 disposed along the lower portion 74 of the test fixture 10. Thus, the apertures 119 located on the rear load frame 38 along the lower portion 74 are visible. In the non-limiting embodiment as shown in FIGS. 1-3, both the front load frames 36 and the rear load frames 38 include a generally C-shaped cross-section, however the frames may have any suitable cross-sectional shape that allows the frames 36, 38 to function as described herein.

Referring now to FIGS. 1-3, the front frame members 32, the rear frame members 34, the front load frames 36, and the rear load frames 38 each cooperate together with one another to define a frame 98 of the test fixture 10. The frame 98 comprises a pair of the front load frames 36, where one of the front load frames 36 is disposed along the lower portion 74 of the test fixture 10 and a remaining one of the front load frames 36 is disposed along the upper portion 76 of the test fixture 10. The frame 98 of the test fixture 10 provides support to the test article 22 when the test article 22 is placed within and secured by the grip plates 40, 42 of the test fixture 10. Moreover, the frame 98 of the test fixture 10 has the requisite strength and stiffness required to provide support to the test article 22 as the vibration device 12 subjects both the test fixture 10 and the test article 22 to vibration. The frame 98 defines the upper portion 76 and the lower portion 74 of the test fixture 10, where the lower portion 74 of the frame 98 is configured to be releasably mounted to the vibration device 12.

Figure 4:
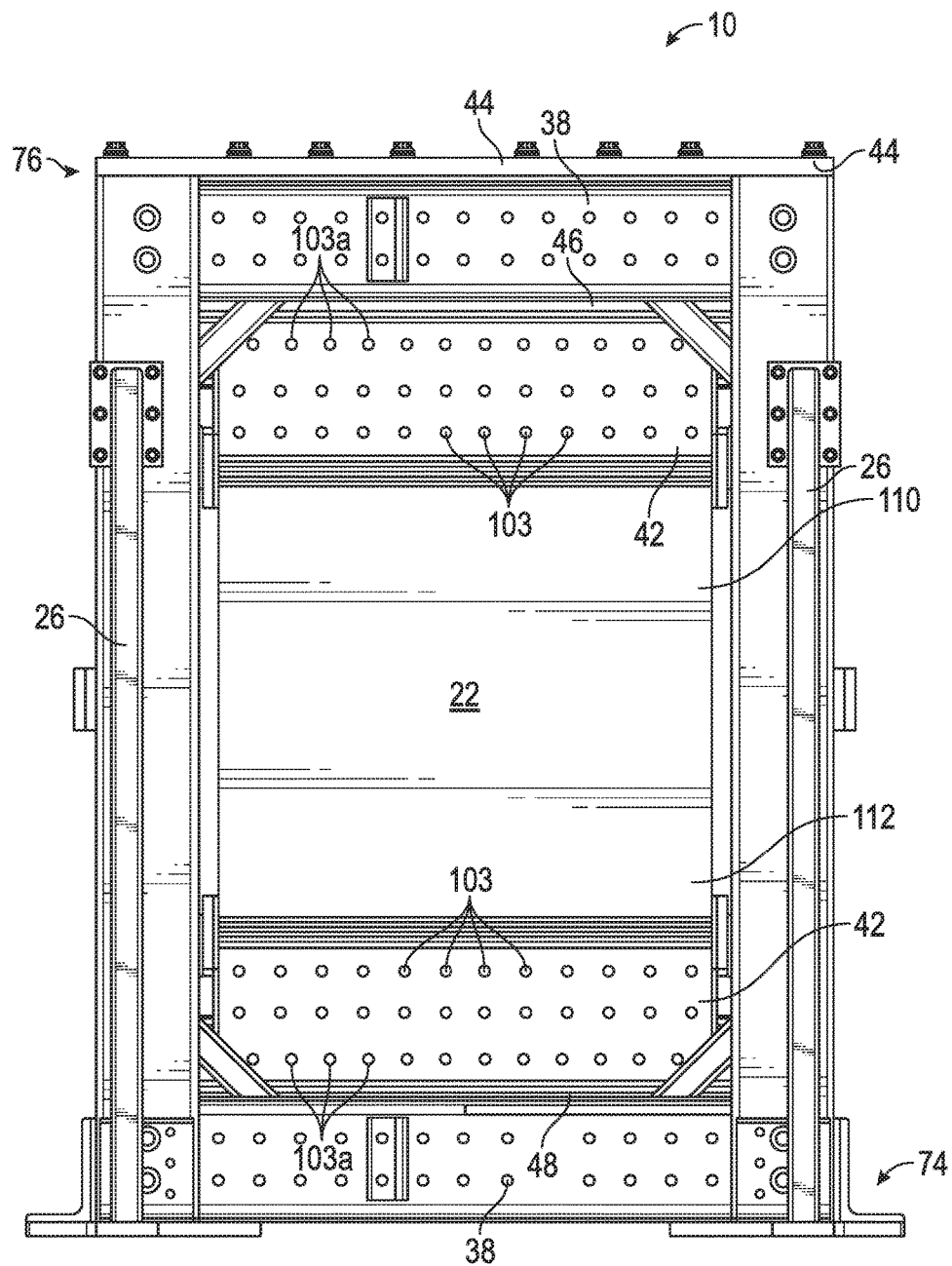
FIG. 4 is a rear view of the test fixture shown in FIG. 1.
Figure 5:
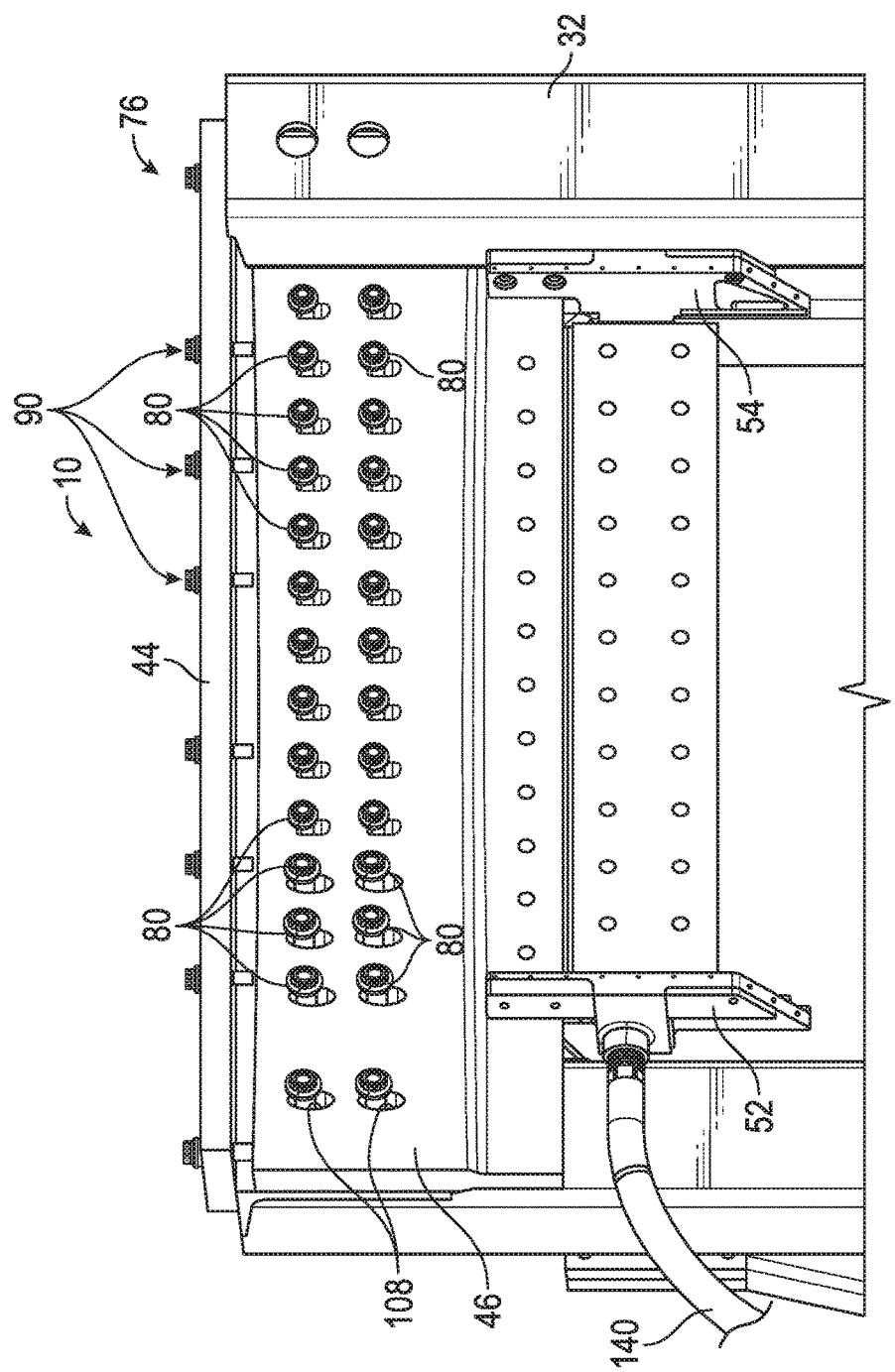
FIG. 5 shows an upper portion of the test fixture shown in FIG. 1, where a front horizontal load frame, a vertical load frame member, and a grip plate are omitted in order to fully view an upper adapter plate and one of the inlet manifolds.

FIG. 5 is an illustration of the upper adapter plate 46 of the test fixture 10, where the front load frame 36 disposed along the upper portion 76 of the test fixture 10 as well as the left front frame member 32 are omitted in order to reveal the upper adapter plate 46, the inlet manifold 52, and an associated tube 140. The fasteners 80, which are engaged with the apertures 78 of the front load frame 36 (FIG. 1), are also engaged with corresponding apertures 108 within the upper adapter plate 46. The apertures 108 of the upper adapter plate 46 include an elongated or oblong profile. The front load frame 36 is located at the upper portion 76 of the frame 98, where the front load frame 36 defines the plurality of apertures 78 that are each shaped to receive a corresponding fastener 80. The upper adapter plate 46 defines the plurality of elongated apertures 108 for receiving one of the corresponding fasteners 80. The elongated profile of the apertures 108 allow for the upper adapter plate 46 to be pulled upwardly as tension is exerted upon the test article 22. The tension is created by adjusting of a plurality of vertical tension bolts 90 mounted to the static tension plate 44, and is described in greater detail below. Although the upper adapter plate 46 includes elongated apertures 108, the lower adapter plate 48 (seen in FIG. 4) includes apertures (not visible in FIG. 4) having a conventional (i.e., substantially round) profile for receiving the fasteners 80. This is because the lower adapter plate 48 remains substantially static, even as tension is exerted upon the test article 22.

Referring to both FIGS. 1 and 3, the static tension plate 44 is positioned along the upper portion 76 of the test fixture 10. Specifically, a bottom surface 84 of the static tension plate 44 abuts or otherwise rests against an upper surface 86 of the front load frame 36 as well as an upper surface 88 of the rear load frame 38. A series of vertical static tension bolts 90 are received by the static tension plate 44. Specifically, the static tension bolts 90 are received by apertures (the apertures are not visible in the figures) disposed along an upper surface 92 of the static tension plate 44. In the non-limiting embodiment as seen in FIG. 1, eight static tension bolts 90 are disposed along the static tension plate 44, however the number of static tension bolts 90 may vary depending upon the specific application.

As seen in FIG. 3, each of the tension bolts 90 includes a first end 100 disposed along the upper surface 86 of the static tension plate 44 and a second end 102. The second end 102 of each tension bolt 90 are received by corresponding apertures (not visible in the figures) disposed along the upper surface 92 of the upper adapter plate 46. Thus, the second end 102 of each tension bolt 90 is attached to the upper adapter plate 46. The tension bolts 90 may include a threaded shank 91 (the threading is not visible in the figures), and the static tension plate 44 may include corresponding through-holes or apertures (also not visible in the figures) for receiving the shank of a corresponding tension bolt 90 in a vertical direction. Thus, the tension bolts 90 are each engaged with a corresponding aperture within the static tension plate 44. In one embodiment, the tension bolts 90 and the corresponding apertures within the static tension plate 44 may include superfine threads, which range between about 32 to about 40 threads per inch. The adjustment mechanism 90 is a plurality of tension bolts 90 that each define a shank 91, where the shank 91 of each tension bolt 90 is connected to the upper adapter plate 46.

The tension bolts 90 and the static tension plate 44 cooperate together to create a tensioner assembly 106. The tensioner assembly 106 exerts a tension force upon the test article 22 by urging the upper adapter plate 46 and the upper grip plates 40, 42 in an upwards direction, and towards the upper portion 76 of the test fixture 10. Specifically, each of the tension bolts 90 act as an adjustment mechanism. As the tension bolts 90 are tightened within their corresponding apertures (not visible in the figures) of the static tension plate 44, the upper adapter plate 46 is urged in an upward direction towards the upper portion 76 of the test fixture 10. As explained in greater detail below, the upper adapter plate 46 is connected to the test article 22. Thus, as the upper adapter plate 46 is urged in an upward direction, this in turn also pulls the test article 22 in the upwards direction as well, thereby exerting a tension load upon the test article 22.

Referring to FIGS. 1-4, the front grip plate 40 and the rear grip plate 42 (FIG. 2) located at the upper portion 76 of the test fixture 10 generally oppose one another and are used to balance the load on test article 22. Similarly, the front grip plate 40 and the rear grip plate 42 located at the lower portion 74 of the test fixture 10 also generally oppose one another. The grip plates 40, 42 at the upper portion 76 of the test fixture 10 are coupled to an upper portion 110 of the test article 22, and the grip plates 40, 42 at the lower portion 74 of the test fixture 10 are coupled to a lower portion 112 of the test article 22. The front grip plates 40 (FIG. 1) both include a series of apertures 104 that are each shaped to receive a corresponding fastener (not shown in the figures). The rear grip plates 42 (FIGS. 2 and 4) each include corresponding apertures 103 that are each shaped to receive a shank of the fasteners engaged with the front grip plates 40.

Figure 6:
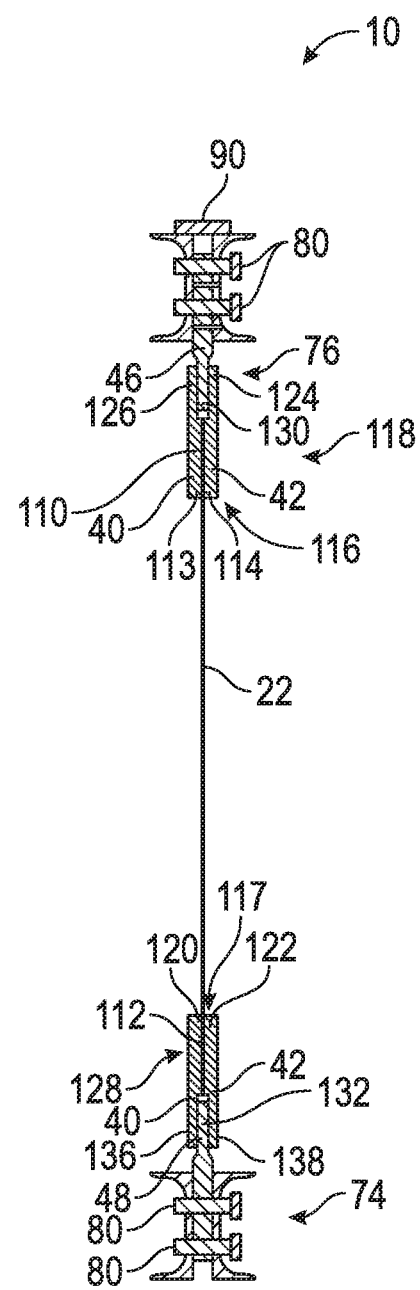
FIG. 6 is a cross-sectioned view of the test fixture taken along section A-A in FIG. 1.

FIG. 6 is a cross-sectioned view of the test fixture 10 taken along section A-A shown in FIG. 1. Referring to both. FIGS. 1 and 6, the test fixture 10 includes an upper grip 118 connected to the upper portion 76 of the frame 98 and a lower grip 128 connected to the lower portion 74 of the frame 98. The upper grip 118 is configured to secure the upper portion 110 of the test article 22 along an upper interface 116, and the lower grip 128 is configured to secure the lower portion 112 of the test article 22 along a lower interface 117. The tensioner assembly 106 is located at the upper portion 76 of the test fixture 10 and is connected to the upper grip 118. The tensioner assembly 106 includes the adjustment mechanism 90 (i.e., the tension bolts), which are configured to urge the upper grip 118 in an upward direction towards the upper portion 76 of the frame 98. The upper grip 118 and the lower grip 128 each include a front grip plate 40 and a rear grip plate 42 that generally oppose one another. The upper adapter plate 46 connects the tensioner assembly 106 to the upper grip 118, where the adjustment mechanism 90 is configured to urge the adapter plate 46 in the upward direction.

The upper portion 110 of the test article 22 is compressed between lower portions 113, 114 of the grip plates 40, 42 located at the upper portion 76 of the test fixture 10. Thus, the lower portions 113, 114 of the grip plates 40, 42 located at the upper portion 76 of the test fixture 10 secure and hold the test article 22 in place along the upper interface 116. The upper interface 116 defines a boundary where the lower portions 113, 114 of the grip plates 40, 42 and the test article 22 engage with one another. The grip plates 40, 42 located at the upper portion 76 of the test fixture 10 cooperate together to create the clamp or grip 118 to secure the upper portion 110 of the test article 22 at the upper interface 116.

Similarly, the lower portion 112 of the test article 22 is clamped between upper ends 120, 122 of the grip plates 40, 42 located at the lower portion 74 of the test fixture 10. Thus, the upper ends 120, 122 of the grip plates 40, 42 located at the lower portion 74 of the test fixture 10 secure and hold the test article 22 in place along the lower interface 117. The grip plates 40, 42 located at the lower portion 74 of the test fixture 10 cooperate together to create the clamp or grip 128 to secure the lower portion 112 of the test article 22 at the lower interface 117. The lower interface 117 defines a boundary where the upper ends 120, 122 of the grip plates 40, 42 and the test article 22 engage with one another.

Referring to FIGS. 4, 5 and 6, a lower end 130 of the upper adapter plate 46 is clamped or secured by upper ends 124, 126 of the grip plates 40, 42 located at the upper portion 76 of the test fixture 10. Accordingly, the upper ends 124, 126 of the grip plates 40, 42 located at the upper portion 76 of the test fixture 10 secure and hold the upper adapter plate 46 in place as shown in FIG. 4 by aperture 103a. Similarly, an upper end 132 of the lower adapter plate 48 are clamped between lower ends 136, 138 of the grip plates 40, 42 located at the lower portion 74 of the test fixture 10. Thus, the lower ends 136, 138 of the grip plates 40, 42 located at the lower portion 74 of the test fixture 10 secure and hold the lower adapter plate 48 in place.

Referring to both FIGS. 1 and 6, when the tension bolts 90 are tightened the upper adapter plate 46 is urged upwardly, in a substantially vertical direction. The grip plates 40, 42 located at the upper portion 76 of the test fixture 10 clamp both the upper adapter plate 46 as well as the upper portion 110 of the test article 22. Thus, movement of the upper adapter plate 46 in the upwards direction also pulls the upper portion 110 of the test article 22 upwardly as well. Furthermore, the grip plates 40, 42 located at the lower portion 74 of the test fixture 10 clamp the lower portion 112 of the test article 22, thereby holding the test article 22 securely in place. Since the upper portion 110 of the test article 22 is pulled upwardly while the lower portion 112 of the test article 22 is held stationary, the test article 22 is placed under tension.

Figure 7:
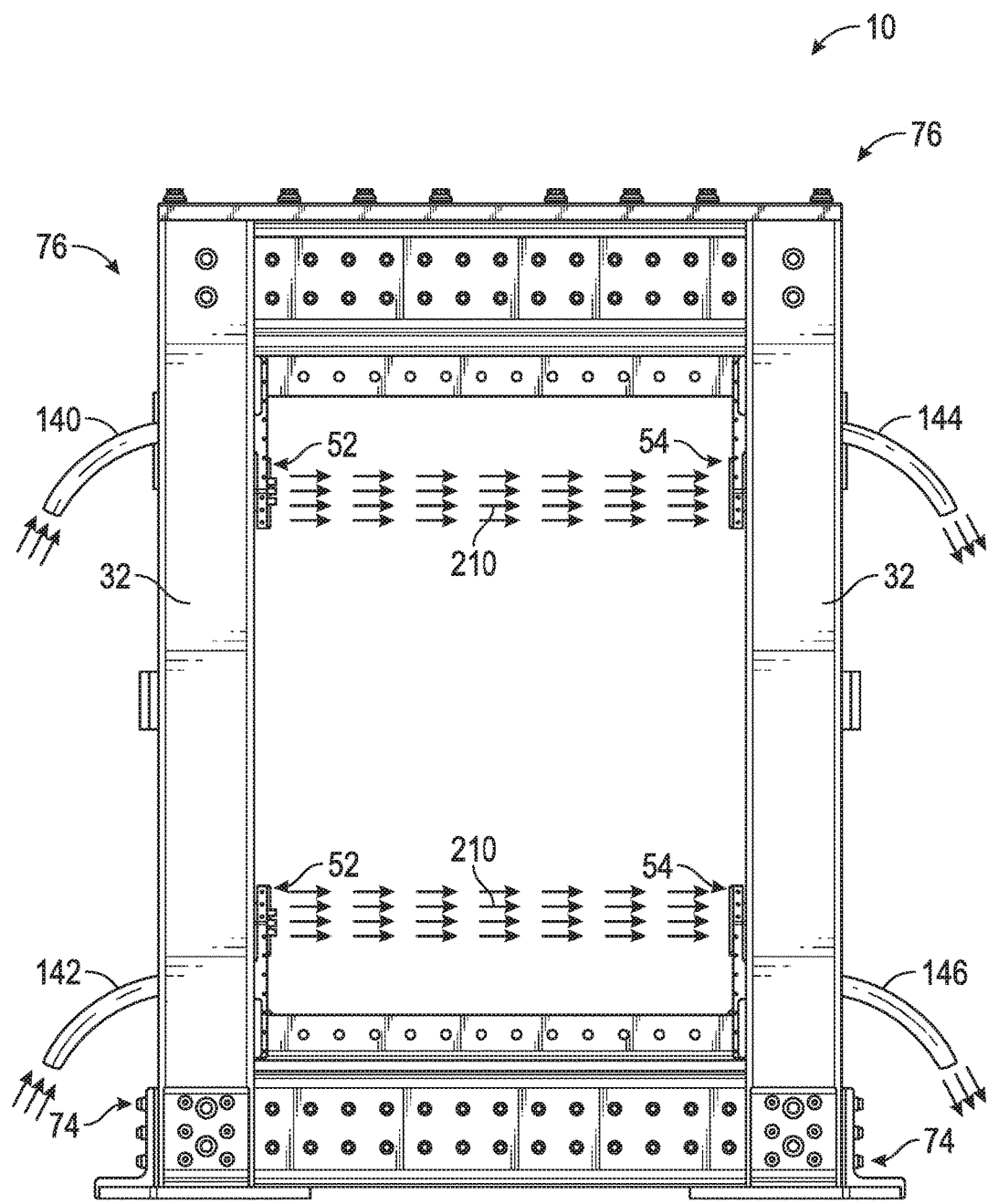
FIG. 7 is a front view illustrating the flow of a cooling medium that is provided to the test fixture in FIG. 1, where the test article, a pair of front grip plates, and a pair of rear grip plates are omitted.

FIG. 7 is a front view of the test fixture 10 where the test article 22, the pair of front grip plates 40, and the rear grip plates 42 are omitted. Both the inlet manifolds 52 and the outlet manifolds 54 are visible in both FIGS. 5 and 7. Referring to both FIGS. 5 and 7, the inlet manifolds 52 and the outlet manifolds 54 provide cooling to the portions of the test fixture 10 that are coupled to the test article 22 (seen in FIG. 1). Specifically, a cooling medium (the direction of flow of the cooling medium is indicated by arrows 210) is transported between the inlet manifolds 52 and the outlet manifolds 54 in order to draw heat and provide cooling. Some examples of the cooling medium that may be used include, for example, cooled gas or air, a cooling liquid such as nitrogen gas or water, or a liquid-gas phase change coolant. As explained below, a cooling liquid or a liquid-gas phase change coolant may be used if cooling tubes (not illustrated in the figures) are provided.

Referring to FIGS. 1 and 7, one of the inlet manifolds 52 may be disposed adjacent to the upper portion 76 of the test fixture 10 and attached or secured to one of the front frame members 32, and a remaining one of the inlet manifolds 52 may be disposed adjacent to the lower portion 74 of the test fixture 10 and secured to a remaining one of the front frame members 32. Similarly, one of the outlet manifolds 54 may be disposed adjacent to the upper portion 76 of the test fixture 10 and secured to one of the front frame members 32, and a remaining one of the outlet manifolds 54 may be disposed adjacent to the lower portion 74 of the test fixture 10 and secured to a remaining front frame member 32. As explained in greater detail below, the inlet manifold 52 positioned adjacent to the upper portion 76 of the test fixture 10 is in fluid communication with the outlet manifold 54 also located adjacent to the upper portion 76 of the test fixture 10 so as to transfer the cooling medium. Similarly, the inlet manifold 72 positioned adjacent to the lower portion 74 of the test fixture 10 is in fluid communication with the outlet manifold 54 also located adjacent to the lower portion 74 of the test fixture 10.

Two inlet tubes 140, 142 are fluidly coupled to a corresponding one of the inlet manifolds 52, and transport the cooling medium from a source (not illustrated) to the test fixture 10. Similarly, two outlet tubes 144, 146 are fluidly coupled to a corresponding one of the outlet manifolds 54. The outlet tubes 144, 146 transport the cooling medium away from the test fixture 10.

Figure 8:
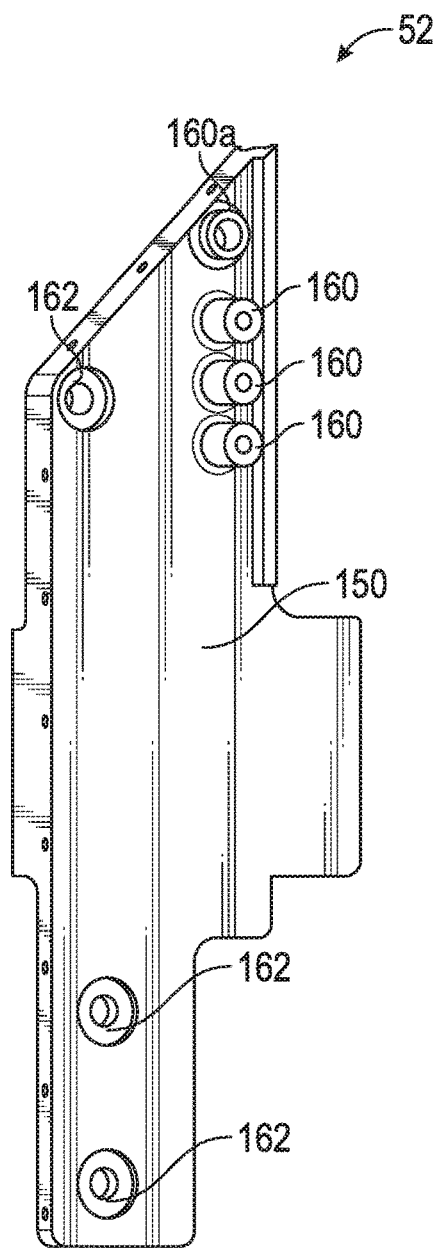
FIG. 8 is an enlarged view of an inner side of an inlet manifold of the test fixture.
Figure 9:
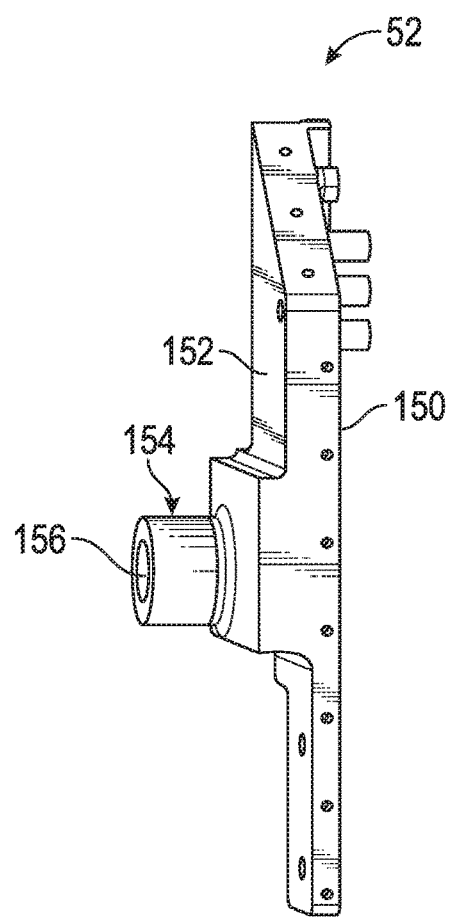
FIG. 9 is an enlarged view of the inlet manifold shown in FIG. 8, viewed along an outer side of the inlet manifold.

FIG. 8 is an enlarged view of one of the inlet manifolds 52, viewed along an inner side 150 of the inlet manifold 52. FIG. 9 is an enlarged view of the inlet manifold 52 shown in FIG. 8, viewed along an outer side 152 of the inlet manifold 52. Referring to both FIGS. 8 and 9, the inlet manifold 52 may include a fitting 154 disposed along the outer side 152. The fitting 154 may be shaped to couple with one of the inlet tubes 140, 142 (seen in FIG. 7). The fitting 154 defines an opening 156 that accepts the cooling medium from a corresponding one of the inlet tubes 140, 142. The opening 156 is fluidly connected to a plurality of inlet openings 160 that are disposed along the inner side 150 of the inlet manifold 52. Thus, the cooling medium may flow from one of the inlet tubes 140, 142 and into the opening 156 of the inlet manifold 52. The cooling medium then exits the inlet manifold from one of the openings 160.

In the embodiment as shown in FIG. 8, three generally circular inlet openings 160 are illustrated. However, this embodiment is merely exemplary in nature, and any number of openings 160 may be included within the inlet manifold 52 as well. Furthermore, the openings 160 may include any type of shape or profile as well such as, for example, elliptical or slotted profiles. In one alternative embodiment, the inlet openings 160 may be shaped as a series of smaller openings so as to create a relatively high-pressure flow of the cooling medium. Furthermore, a selected opening 160a of the inlet manifold 52 may be larger in size when compared to the remaining openings 160 of the inlet manifold 52. The opening 160a may be provided in order to create a relatively low pressure flow of cooling medium. The inlet manifold 52 may also define one or more apertures 162 for receiving a fastener that secures the inlet manifold 52 to the test fixture 10.

Figure 10:
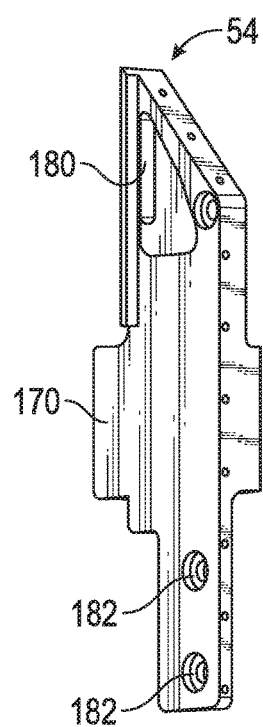
FIG. 10 is an enlarged view of an inner side of an outlet manifold of the test fixture.
Figure 11:
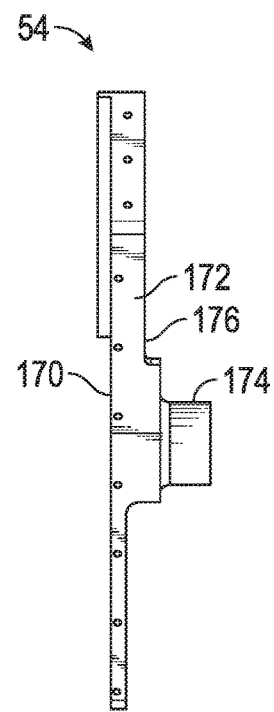
FIG. 11 is an enlarged view of the outlet manifold shown in FIG. 10, viewed along an outer side of the outlet manifold.

FIG. 10 is an enlarged view of one of the outlet manifolds 54 viewed along an inner side 170. FIG. 11 is an enlarged view of the outlet manifold 54 shown in FIG. 10, viewed along a front side 172 of the outlet manifold 54. Referring to both FIGS. 10 and 11, the outlet manifold 54 may include a fitting 174 disposed along an outer side 176. The fitting 174 may be shaped to couple with one of the outlet tubes 144, 146 (seen in FIG. 7). The fitting 174 defines an opening (not visible in the figures) that accepts the cooling medium from a corresponding one of the inlet manifolds 52. The opening of the fitting 174 is fluidly connected to an opening 180 disposed along the inner side 170 of the outlet manifold 54. Thus, the cooling medium flows into the opening 180 of the outlet manifold 54, and then exits the outlet manifold 54 from the opening within the fitting 174. In the non-limiting embodiment as shown in FIG. 10, the opening 180 includes a generally slot-shaped or elliptical profile. However, other profiles may be used as well such as, for example, a trapezoidal profile. The overall size or area of the opening 180 may also be based upon specific target flow characteristics of the cooling medium. Furthermore, although FIG. 10 illustrates a single opening 180, the outlet manifold 54 may include multiple openings as well.

Figure 12:
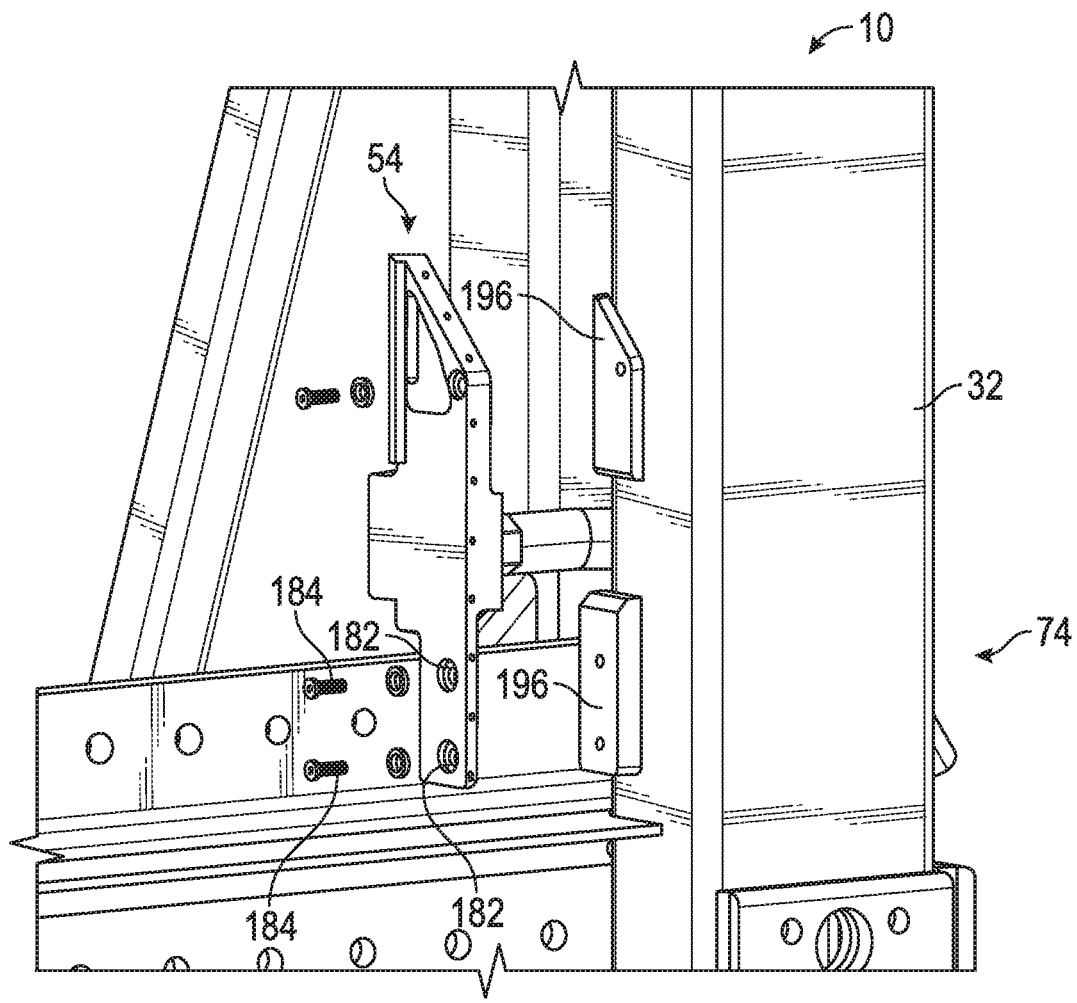
FIG. 12 is an exploded view of the outlet manifold and attachment bolts disposed adjacent to a lower portion of the test fixture.

FIG. 12 is an exploded view of one of the outlet manifolds 54 disposed adjacent to the lower portion 74 of the test fixture 10. The outlet manifold 54 defines one or more apertures 182 for receiving a corresponding fastener 184. The outlet manifold 54 may be secured to one of the front frame members 32 by a set of brackets 196. Although FIG. 12 illustrates only one of the outlet manifolds 54, the remaining outlet manifold 54 may be secured to the test fixture 10 in a similar manner. The inlet manifolds 52 (FIGS. 8-9) may also be secured to the test fixture 10 using fasteners and brackets as well. Finally, while FIG. 12 illustrates the outlet manifold 54 attached to one of the front frame members 32 by brackets 196 this embodiment is merely exemplary in nature. Indeed, the inlet and outlet manifolds 52, 54 may be attached to the test fixture 10 during a variety of different approaches.

Figure 13:
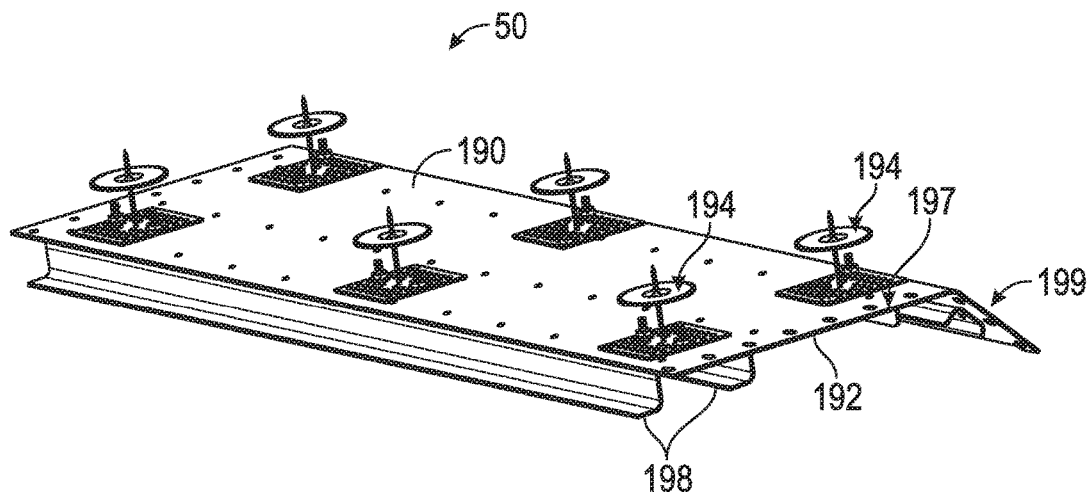
FIG. 13 illustrates an outer side of a heat shield.
Figure 14:
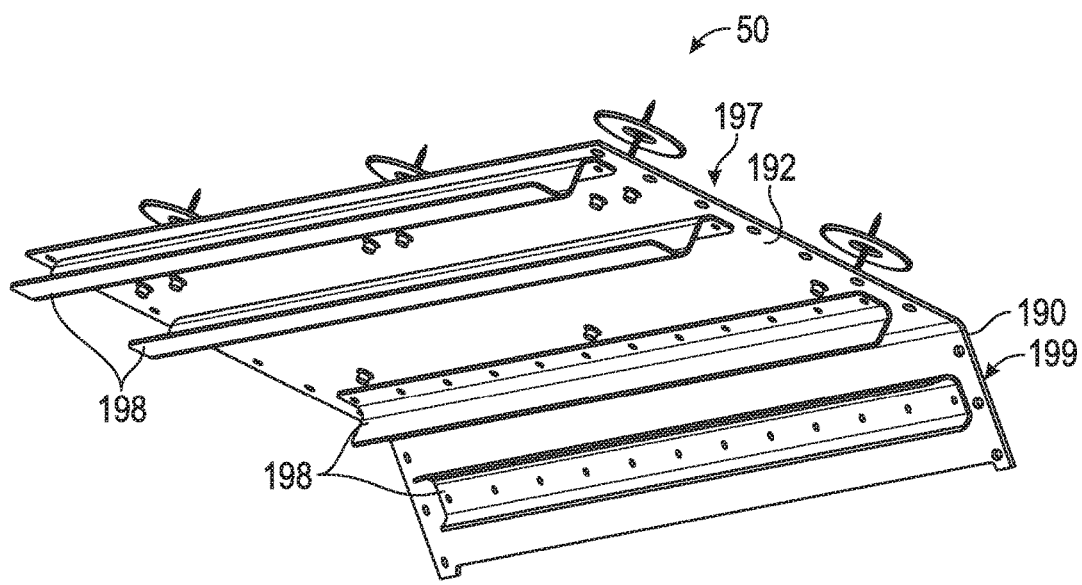
FIG. 14 illustrates an inner side of the heat shield shown in FIG. 13.

FIGS. 13-14 illustrate one of the heat shields 50, where FIG. 13 is a view of an outer side 190 of the heat shield 50 and FIG. 14 is a view of an inner side 192 of the heat shield 50. In the embodiment as shown in FIG. 13, one or more tie clips 194 may be disposed along the outer side 190 of the heat shield 50. The tie clips 194 may be used to secure an outer insulation blanket 212 (seen in FIG. 16). The inner side 192 of the heat shield 50 may include one or more louvers 198. The louvers 198 project away from the inner side of the heat shield 50, and may provide stiffening to the heat shield 50. The stiffness provided by the louvers 198 may be especially beneficial when the test fixture 10 undergoes vibration testing. As explained in greater detail below, the heat shield 50 insulates the front grip plates 40 (FIG. 1), the fasteners engaged with the front grip plates 40 (not visible in the figures), and the fastener apertures 104 define by the front grip plates 40. Specifically, the heat shield 50 provides insulation from the elevated temperatures generated by the heating device 53 (seen in FIG. 3). The heat shield 50 may be shaped to define a flat portion 197 and an angled portion 199. The angled portion 199 of the heat shield 50 may be formed as a lip or an edge that projects at an angle relative to the flat portion 197 of the heat shield 50.

Figure 15:
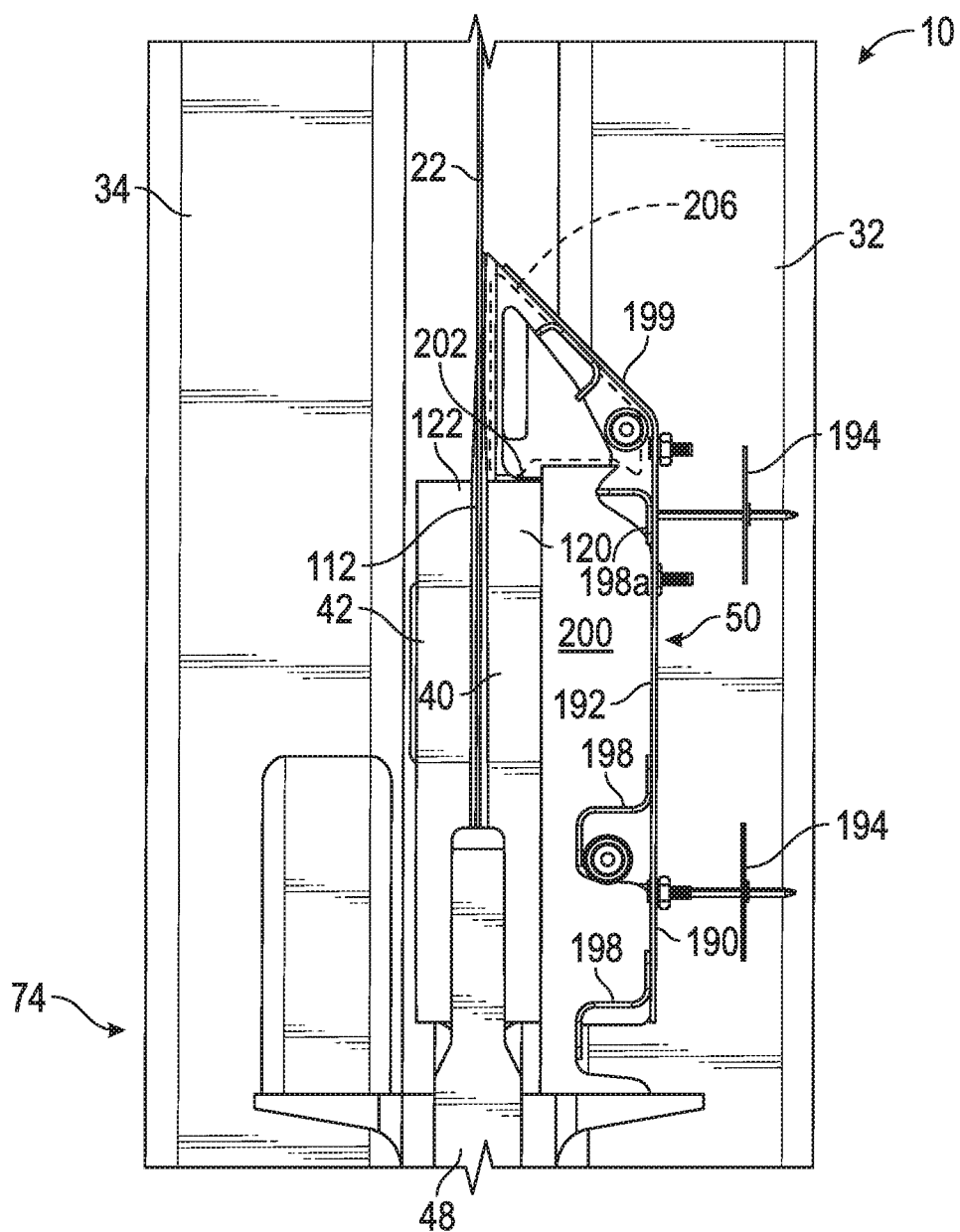
FIG. 15 is a cross-sectioned view of the lower portion of the test fixture including the heat shield shown in FIGS. 13-14, where a sheet of insulation is disposed between an inner side of the heat shield and the front grip plate and an outer insulation blanket is omitted.

FIG. 15 is a cross-sectioned view of the lower portion 74 of the test fixture 10 including the heat shield 50. In the embodiment as shown, the heat shield 50 is positioned to cover and insulate the entire front grip plate 40. However, in another approach only the upper end 120 of the front grip plate 40 may be insulated by the heat shield 50. As seen in FIG. 15, a sheet of insulation 200 may be disposed between the inner side 192 of the heat shield 50 and the front grip plate 40. The louvers 198 of the heat shield 50 pinch or compress the insulation 200, thereby securing the insulation 200 in place between the heat shield 50 and the front grip plate 40. The insulation 200 may be any type of insulation compressed by the louvers 198 such as, for example, a high-temperature ceramic fiber blanket. The heat shield 50 and the insulation 200 both protect and insulate the front grip plate 40 and the fasteners associated with the front grip plate 40 from the elevated temperatures generated by the heating device 53 (FIG. 3) during testing. The insulation 200 also creates a substantially fluid-tight seal along a portion compressed by a selected stiffener 198a.

Referring now to FIGS. 1, 7-11, and 15, cooling of the upper end 120 of the front grip plate 40 as well as lower portion 112 of the test article 22 by the cooling medium will now be described. The inlet manifold 52, the outlet manifold 54, and the heat shield 50 cooperate together to create a cooling assembly 204 for transporting the cooling medium across the upper end 120 of the front grip plate 40 as well as lower portion 112 of the test article 22. The cooling medium first flows into the inlet manifold 52 by way of the inlet tube 142 (FIG. 7). The cooling medium then exits the inlet manifold 52 through the openings 160 (FIG. 8).

The cooling assembly 204 is configured to transport the cooling medium across at least one of the upper interface 116 and the lower interface 117 (seen in FIG. 1). The cooling assembly 204 includes an inlet manifold 52, where the inlet manifold 52 defines at least one opening 160 to direct the cooling medium across one of the upper interface 116 and the lower interface 117. The cooling assembly 204 also includes the outlet manifold 54, where the outlet manifold 54 defines at least one opening 180 in fluid communication with the opening 160 of the inlet manifold 52. Moreover, the cooling assembly 204 includes at least one heat shield 50 positioned to insulate at least one of the upper grip 118 and the lower grip 128.

As seen in FIG. 15, the insulation 200 compressed between the heat shield 50, the selected louver 198a of the front grip plate 40, an upper surface 202 of the front grip plate 40, and the angled portion 199 of the heat shield 50 along the inner side 192 cooperate together to define a passage 206, which is shown in dashed line. The cooling medium flows out of the opening 160 of the inlet manifold 52 and into the passage 206. The cooling medium then enters the opening 180 of the outlet manifold 54. In the embodiment as shown in FIG. 15, the passage 206 includes a substantially triangular cross-section, however this illustration is merely exemplary in nature and any other cross-sectional shape may be used as well. The insulation 200 is secured between the heat shield 50 and at least one of the upper grip 118 and the lower grip 128 (FIG. 6), where a portion of the heat shield 50 and one of the upper grip 118 and the lower grip 128 cooperate to define a passage 206 for the cooling medium to travel within.

In the embodiment as shown in the figures, the cooling medium is a gas. However, in the event the cooling medium is a liquid or a liquid-gas phase change coolant, then piping or tubes (not illustrated in the figures) are provided within the passage 206. The tubes transport the cooling medium between the openings 160 of the inlet manifold 52 and the opening 180 of the outlet manifold 54.

The openings 160 of the inlet manifold 52 directs the cooling medium in transverse direction 210 (FIG. 7) within the passage 206. The cooling medium travels along the upper end 120 of the front grip plate 40 as well as lower portion 112 of the test article 22 to draw heat. The upper end 120 of the front grip plate 40 as well as lower portion 112 of the test article 22 experience elevated temperatures generated by the heating device 53 (FIG. 3) during testing. The cooling medium then exits the passage 206 and into the opening 180 of the outlet manifold 54. The cooling medium then exits the outlet manifold 54 from the opening within the fitting 174, and into the outlet tube 146.

While the lower portion 74 of the test fixture 10 is illustrated in the figures as including the heat shield 50 and various cooling features, the upper portion 76 of the test fixture 10 may also include a substantially similar cooling structure as well. Moreover, as seen in FIG. 19, the heat shield 50 may also be included along the upper portion 76 of the test fixture 10 as well. Furthermore, another cooling system may also be used to cool the front frame members 32 as well. Specifically, referring back to FIG. 1, the cooling medium may also be provided within an internal channel (not included in the figures) of the front frame members 32. The cooling medium is introduced by apertures 214 located along the front frame members 32.

Figure 16:
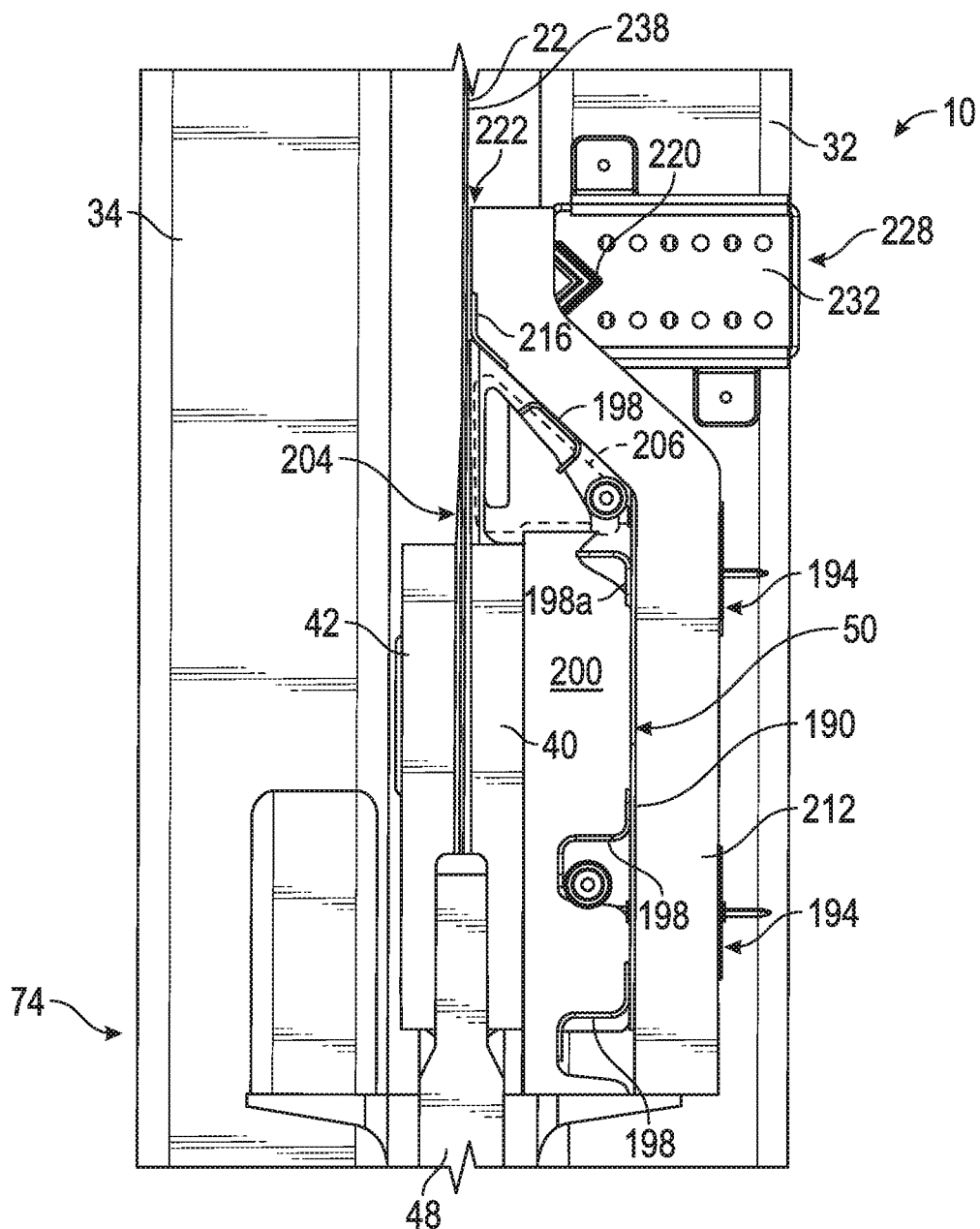
FIG. 16 is an illustration of the test fixture shown in FIG. 15 including the insulation blanket disposed along the outer surface of the heat shield.

FIG. 16 is a cross-sectioned view of the lower portion 74 of the test fixture 10, where the outer insulation blanket 212 is disposed along the outer side 190 of the heat shield 50. The tie clips 194 (best seen in FIG. 13) may be used to retain the outer insulation blanket 212. The outer insulation blanket 212 provides further protection and insulation from the elevated temperatures generated by the heating device 53 shown in FIG. 3 during testing. The outer insulation blanket 212 is compressed tightly against the test article 22 by an insulation hold-down beam 220. The hold-down beam 220 may be part of a bracket assembly 228. The bracket assembly 228 may further include a pair of adjustment brackets 232 (only one of the adjustment brackets 232 is visible in FIG. 16). Referring to both FIGS. 16 and 17, each of the adjustment brackets 232 positions the hold-down beam 220 relative to an outer surface 238 of the test article 22.

As seen in FIG. 16, the hold-down beam 220 presses against or compresses the outer insulation blanket 212 in order to create a substantially fluid-tight seal between the outer insulation blanket 212 and the outer surface 238 of the test article 22. The seal between the insulation blanket 212 and the test article 22 substantially prevents the ingression of flame and/or hot gases into the passage 206. Thus, the insulation blanket 212 is secured to the outer side 190 of the heat shield 50 and the hold-down beam 220 is secured to the test fixture 10 and is compressed against the outer surface 238 of the test article 22 to create a substantially fluid-tight seal. In one embodiment, the insulation blanket 212 may further include a flexible gas seal 216 disposed along an interface 218 between the outer insulation blanket 212 and the outer surface 238 of the test article 22. The flexible gas seal 216 is constructed of a relatively flexible material such as, for example, a high-temperature elastomer that may withstand the elevated temperatures that the interface 218 may experience during various tests. The flexible gas seal 216 creates a seal between the outer insulation blanket 212 and the outer surface 238 of the test article 22.

Figure 17:
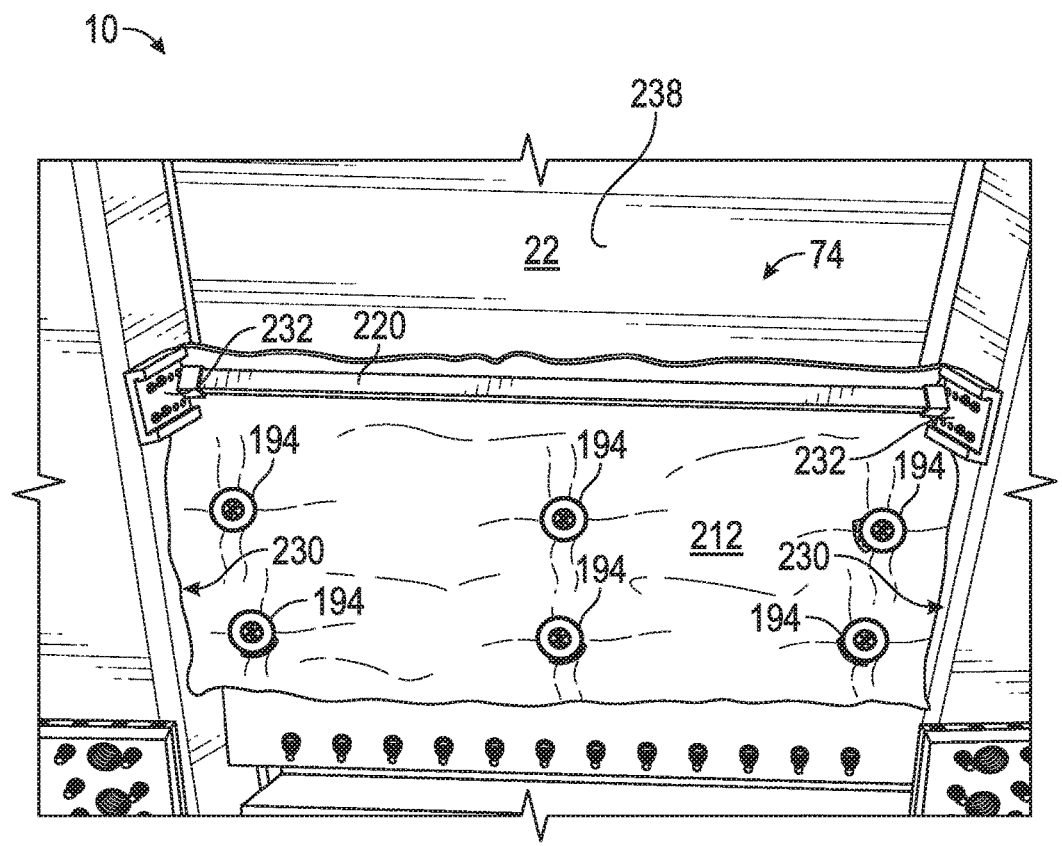
FIG. 17 illustrates an exterior of the lower portion of the test fixture including the insulation blanket shown in FIG. 16.

FIG. 17 illustrates the exterior of the lower portion 74 of the test fixture 10, where the insulation blanket 212 is included. Referring to both FIGS. 16 and 17, the hold-down beam 220 is secured against the insulation blanket 212, between a seam or gap 222 between the test article 22 and the heat shield 50. The hold-down beam 220 is assembled to the test fixture 10 prior to the outer insulation blanket 212. The hold-down beam 220 extends in a transverse direction along the insulation blanket 212, and substantially prevents the cooling medium from exiting the passage 206. In an alternative embodiment, a sealant such as, for example, silicone may be disposed along the gap 222 to provide sealing instead. Moreover, in one embodiment sealant may also be placed along opposing sides 230 of the insulation blanket 212 as well to substantially prevent the ingression of heat generated by the heating device 53 (FIG. 3).

Figure 18:
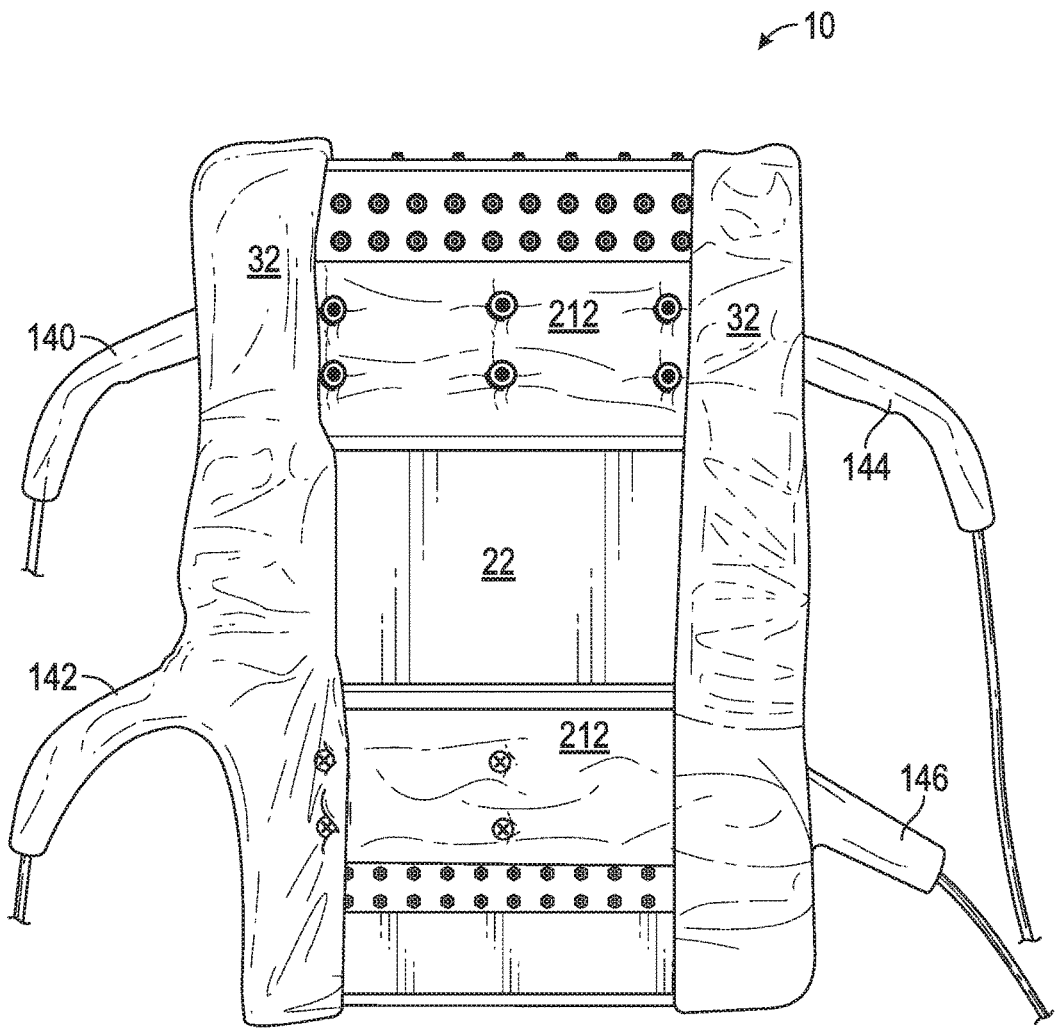
FIG. 18 illustrates insulation placed over a pair of front vertical frame members, inlet tubes, outlet tubes, and the heat shields of the test fixture.

FIG. 18 is an illustration of the test fixture 10 where insulation has been placed along both the front frame members 32, the inlet tubes 140, 142, and the outlet tubes 144, 146. The insulation may be used to protect and insulate both the front frame members 32, the inlet tubes 140, 142, and the outlet tubes 144, 146 from the heat generated by the heating device 53 (FIG. 3).

FIGS. 19 and 20 illustrate the test fixture 10 securing a test article comprised of two discrete sections 322*a* and 322*b*. Specifically, FIG. 19 is a front view of the test fixture 10, where the insulation blanket 212 is omitted. The two test articles 322*a* and 322*b* are disposed beside one another. A seam or gap 330 is defined between a side edge 332 of the test article 322*a* and a side edge 334 of the test article 322*b*.

As seen in FIG. 19, in one embodiment a sealant bead 340 is provided along a portion of the gap 330. Specifically, the sealant bead 340 is provided along the gap 330 adjacent to the heat shield 50 positioned at the upper portion 76, as well as the heat shield 50 positioned at the lower portion 74 of the test fixture 10. The sealant bead 340 may also be provided along an edge 316 of the heat shield 50 positioned at the upper portion 76 of the test fixture 10 and adjacent to the two test articles 322*a*, 322*b* as well as an edge 318 of the heat shield 50 positioned at the lower portion 74 of the test fixture 10 and adjacent to the two test articles 322*a*, 322*b*. In one embodiment the sealant bead 340 disposed along the seam or gap 330 may be constructed of a sealing material rated at a higher temperature when compared to the material of the sealant beads 340 located along the edges 316, 318 of the heat shield 50.

Turning now to FIG. 20, a support member 342 is positioned along a back side 344 of the two test articles 322*a* and 322*b*. Specifically, the support member 342 extends in a longitudinal direction, and directly opposite to the gap 330 created by the two test articles 322*a* and 322*b*. The support member 342 may be secured to the test fixture by an upper bracket 350 and a lower bracket 352. The upper bracket 350 may be secured to an upper end portion 360 of the support member 342. In the exemplary embodiment as shown in FIG. 20, the bracket 350 may be secured to the test fixture 10 by the fasteners 80 received by the rear load frame 38 positioned at the upper portion 76 of the test fixture 10. Similarly, the lower bracket 352 may be secured to the test fixture 10 by the fasteners 80 received by the rear load frame 38 positioned at the lower portion 74 of the test fixture 10. Although FIG. 20 illustrates the upper and lower brackets 350, 352, a variety of other fastening approaches may be used as well.

Figure 21:
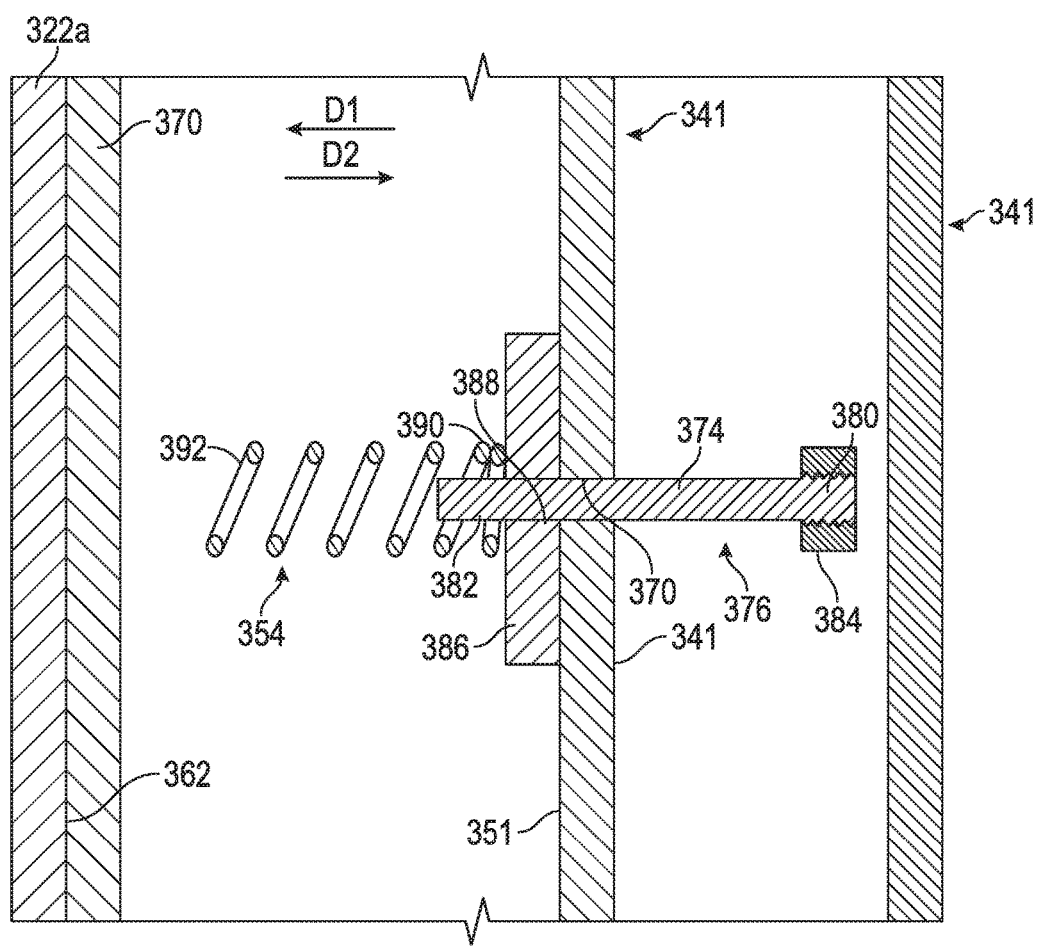
FIG. 21 is an enlarged, cross-sectioned view of a portion of the test article and the support member shown in FIG. 20, where a biasing element exerts a force against the two sections of the test article.

The support member 342 provides support for the two test articles 322*a* and 322*b* along the gap 330. Specifically, the support member 342 defines a flange or edge 341 that also extends in the longitudinal direction. FIG. 21 is an enlarged cross-sectioned view of a portion of the test article 322*a* and the edge 341 of the support member 342 shown in FIG. 20. Referring now to both FIGS. 20 and 21, the edge 341 of the support member 342 defines a surface 351 that generally opposes the gap 330 defined by the two test articles 322*a* and 322*b*. As seen in FIG. 21, one or more biasing elements 354 are disposed along the surface 351 of the edge 341 of the support member 342. Although FIG. 21 illustrates a single biasing element 354, a plurality of biasing elements 35 are disposed along a length L of the edge 341 of the support member 342 (FIG. 20). Furthermore, although FIG. 21 illustrates the biasing element 354 as a coil spring, this illustration is merely exemplary in nature, and a variety of biasing elements that exert a force in a direction D1 towards the test articles 322*a* and 322*b* may be used as well. Thus, the support member 342 extends in the longitudinal direction between the pair of front load frames 36, where the support member 342 defines the edge 341 having a series of biasing elements 354 extending along the length L of the edge 341.

Continuing to refer to both FIGS. 20 and 21, a support or filler panel 372 (visible only in FIG. 21) may be positioned along a back side 362 of the two test articles 322*a* and 322*b*, along the gap 330. The edge 341 defines a series of apertures 370 that extend along the length L of the edge 341 (FIG. 20). Each aperture 370 is shaped to receive a corresponding shank 374 of a bolt 376 (FIG. 21). The shank 374 of the bolt 376 defines a first end portion 380 and a second end portion 382. A nut 384 is threadingly engaged with the first end portion 380 of the shank 374, and the biasing element 354 is attached to the second end portion 382 of the shank 374. A plate 386 defines an aperture 388 shaped to receive the second end portion 382 of the shank 374. A first end 390 of the biasing member 354 is attached to the plate 386, and a second end 392 of the biasing element 354 opposes the filler panel 372. The biasing element 354 may be fixedly attached to the plate 386 by a joining method such as, for example, welding.

The position of the second end 392 of the biasing element 354 relative to the test articles 322*a* and 322*b* is adjustable. In one approach, the nut 384 may be rotated about the shank 374 of the bolt 376 in a clockwise or counterclockwise direction in order to move the bolt 376 in a lateral direction. Specifically, the bolt 376 may move either towards the test articles 322*a* and 322*b* in the direction D1, or away from the test articles 322*a* and 322*b* in a direction D2. In another approach, the position of the second end 392 of the biasing element 354 may be moved in the directions D1 and D2 by adjusting the position of the support member 342 relative to the test articles 322*a*, 322*b* by the brackets 350, 352 (seen in FIG. 21). Although FIG. 21 does not illustrate the second end 392 of the biasing element 354 in contact with the filler panel 372, during testing the second end 392 makes contact with and exerts a biasing force against the filler panel 372 and the test articles 322*a* and 322*b*. Thus, the force exerted by the biasing element 354 upon the two test articles 322*a* and 322*b* provides support and stability along the gap 330.

Figure 22:
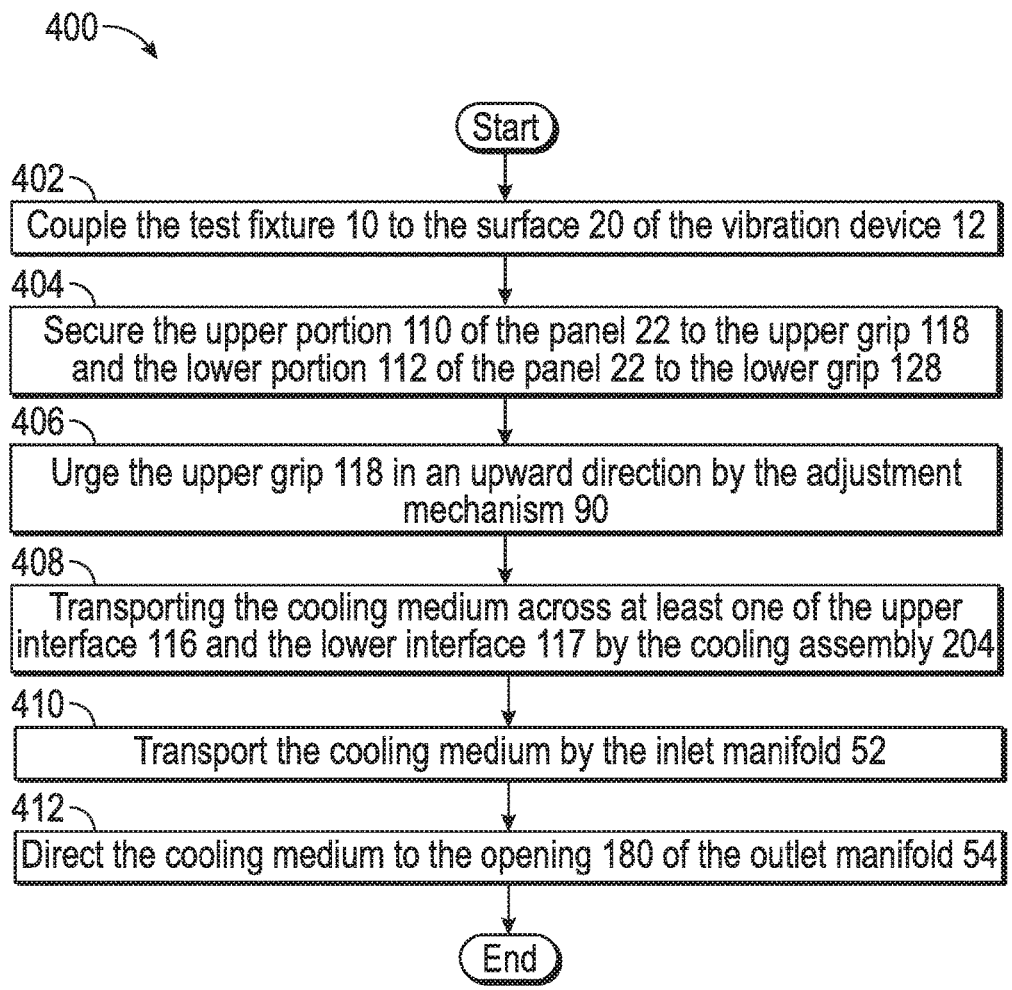
FIG. 22 is a process flow diagram illustrating an exemplary method of cooling the test panel.

FIG. 22 is a process flow diagram illustrating an exemplary method 400 of cooling the test panel 22. Referring now to FIGS. 1 and 23, method 400 may begin at block 402. In block 402, the test fixture 10 is coupled to the surface 20 of the vibration device 12. The test fixture 10 includes the frame 98 defining the upper portion 76 and the lower portion 74. The test fixture 10 is releasably mounted to the surface 20 of the vibration device 12 at the lower portion 74 of the frame 98. Method 400 may then proceed to block 404.

In block 404, the upper portion 110 of the panel is secured) the upper grip 118 along the upper interface 116, and the lower portion 112 of the panel 22 to the lower grip 128 along the lower interface 117. The upper grip 118 is connected to the upper portion 76 of the frame 98 and the lower grip 128 is connected to the lower portion 74 of the frame 98. Method 400 may then proceed to block 406.

In block 406, the upper grip 118 is urged in an upward direction and towards the upper portion 76 of the panel 22 by the adjustment mechanism 90 of the tensioner assembly 106. The tensioner assembly 106 is located at the upper portion 76 of the test fixture 10 and is connected to the upper grip 118. Method 400 may then proceed to block 408.

In block 408, the cooling medium is transported across at least one of the upper interface 116 and the lower interface 117 by the cooling assembly 204. Method 400 may then proceed to block 410.

In block 410, the cooling medium is directed across one of the upper interface 116 and the lower interface 117 by an inlet manifold 52. The inlet manifold 52 defines at least one opening 160 (FIG. 8). Method 400 may then proceed to block 412.

In block 412, the cooling medium directed across one of the upper interface 116 and the lower interface 117 is directed to the opening 180 defined by the outlet manifold 54 (FIG. 10). Method 400 may then terminate.

Referring generally to the figures, the disclosed test fixture accommodates subjecting a test article to tension, vibration, and heat simultaneously. The test fixture may withstand the elevated temperatures that are usually experienced during testing. Furthermore, the test fixture may also include a relatively lightweight and compact profile sufficient to accommodate the vibrations typically experienced during testing. For example, in one embodiment the test fixture may include an overall weight of about 340 kilograms (750 pounds). A relatively lightweight and compact profile may be especially advantageous in situations where a vibration device, such as a vibration table, is unable to accommodate a very heavy or bulky test fixture. The disclosed test fixture may also include the requisite stiffness and strength required to accommodate the loads experienced during testing. Furthermore, the test fixture may include various features that insulate various components of the test fixture. In addition to providing insulation, the test fixture may also include cooling features for providing active cooling to a portion of the test fixture that secures the test article. The cooling features may allow for the test fixture to secure and maintain tension upon the test article as the test article is subjected to elevated temperatures during testing. In some instances, the elevated temperatures may be greater than the minimum temperature required to reduce the load necessary to deform the material of the test article.

While the forms of apparatus and methods herein described constitute preferred examples of this invention, it is to be understood that the invention is not limited to these precise forms of apparatus and methods, and the changes may be made therein without departing from the scope of the invention.

What is claimed is:

1. A test fixture for securing a test article, the test fixture comprising:
a frame defining an upper portion and a lower portion, wherein the lower portion of the frame is configured to be releasably mounted to a vibration device;
an upper grip connected to the upper portion of the frame and a lower grip connected to the lower portion of the frame, wherein the upper grip is configured to secure an upper portion of the test article along an upper interface, the lower grip is configured to secure a lower portion of the test article along a lower interface, and the upper interface and the lower interface both define a boundary wherein the test article is engaged with either the upper grip or the lower grip;
a tensioner assembly located at the upper portion of the test fixture, wherein the tensioner assembly is connected to the upper grip and includes an adjustment mechanism configured to urge the upper grip in an upward direction towards the upper portion of the frame;
an upper adapter plate connecting the tensioner assembly to the upper grip, wherein the upper adapter plate defines a plurality of elongated apertures that each receive a corresponding upper fastener, and wherein the elongated profile of the apertures allow for the upper adapter plate to be pulled upwardly as tension is exerted upon the test article;
a lower adapter plate defining a plurality of substantially round apertures for each receiving a corresponding lower fastener, wherein the lower adapter plate remains substantially static as tension is exerted upon the test article;
a cooling assembly configured to transport a cooling medium across at least one of the upper interface and the lower interface;
an inlet manifold defining at least one opening to direct the cooling medium across one of the upper interface and the lower interface; and
a pair of front frame members each positioned at an opposing side of the test fixture, wherein the inlet manifold is secured to one of the front frame members.

2. The test fixture of claim 1, wherein the cooling assembly includes an outlet manifold, and wherein the outlet manifold defines at least one opening in fluid communication with the at least one opening of the inlet manifold.

3. The test fixture of claim 2, wherein the cooling assembly includes a pair of front frame members each positioned at an opposing side of the test fixture, and wherein the inlet manifold is secured to one of the front frame members and the outlet manifold is secured to a remaining one of the front frame members.

4. The test fixture of claim 1, wherein the cooling assembly includes at least one heat shield positioned to insulate at least one of the upper grip and the lower grip.

5. The test fixture of claim 4, comprising insulation secured between the heat shield and at least one of the upper grip and the lower grip, wherein a portion of the heat shield and one of the upper grip and the lower grip cooperate to define a passage for the cooling medium to travel within.

6. The test fixture of claim 4, comprising an insulation blanket and a beam, wherein the beam compresses the insulation blanket to create a substantially fluid-tight seal against the insulation blanket and an outer surface of the test article.

7. The test fixture of claim 1, wherein the upper grip and the lower grip each include a front grip plate and a rear grip plate that generally oppose one another.

8. The test fixture of claim 1, wherein the adjustment mechanism is configured to urge the upper adapter plate in the upward direction.

9. The test fixture of claim 8, wherein the upper fasteners comprise a plurality of tension bolts that each define a shank, and wherein the shank of each tension bolt is connected to the upper adapter plate such that as the tension bolts are tightened the upper adapter plate is urged in the upward direction.

10. The test fixture of claim 8, comprising a front load frame located at the upper portion of the frame, wherein the front load frame defines the plurality of elongated apertures for each receiving a corresponding upper fastener.

11. The test fixture of claim 1, wherein the cooling medium is at least one of a cooled gas, cooled air, a cooling liquid, and a liquid-gas phase change coolant.

12. The test fixture of claim 1, wherein the frame comprises a pair of front load frames, wherein one of the front load frames is disposed along the lower portion of the test fixture, and a remaining one of the front load frames is disposed along an upper portion of the test fixture.

13. The test fixture of claim 12, comprising a support member extending in a longitudinal direction between the pair of front load frames, wherein the support member defines an edge having a series of biasing elements extending along a length of the edge.

14. A system for testing a test article, the system comprising:
   a vibration device defining a surface; and
   a test fixture coupled to the surface of the vibration device, comprising:
      a frame defining an upper portion and a lower portion, wherein the lower portion of the frame is releasably mounted to the surface of the vibration device;
      an upper grip connected to the upper portion of the frame and a lower grip connected to the lower portion of the frame, wherein the upper grip is configured to secure an upper portion of the test article along an upper interface, the lower grip is configured to secure a lower portion of the test article along a lower interface, and the upper interface and the lower interface both define a boundary wherein the test article is engaged with either the upper grip or the lower grip;
      a tensioner assembly located at the upper portion of the test fixture, wherein the tensioner assembly is connected to the upper grip and includes an adjustment mechanism configured to urge the upper grip in an upward direction towards the upper portion of the frame;
      an upper adapter plate connecting the tensioner assembly to the upper grip, wherein the upper adapter plate defines a plurality of elongated apertures that each receive a corresponding upper fastener, wherein the elongated profile of the apertures allow for the upper adapter plate to be pulled upwardly as tension is exerted upon the test article;
      a lower adapter plate defining a plurality of substantially round apertures for each receiving a corresponding lower fastener, wherein the lower adapter plate remains substantially static as tension is exerted upon the test article;
      a cooling assembly configured to transport a cooling medium across at least one of the upper interface and the lower interface;
      an inlet manifold defining at least one opening to direct the cooling medium across one of the upper interface and the lower interface; and
      a pair of front frame members each positioned at an opposing side of the test fixture, wherein the inlet manifold is secured to one of the front frame members.

15. The system of claim 14, wherein the cooling assembly includes an outlet manifold defining at least one opening in fluid communication with the at least one opening of the inlet manifold.

16. The system of claim 14, wherein the cooling assembly includes at least one heat shield positioned to insulate at least one of the upper grip and the lower grip.

17. A method of testing a panel, the method comprising:
   coupling a test fixture to a surface of a vibration device, wherein the test fixture includes a frame defining an upper portion and a lower portion, and wherein the test fixture is releasably mounted to the surface at the lower portion of the frame;
   securing an upper portion of the panel to an upper grip along an upper interface, and a lower portion of the panel to a lower grip along a lower interface, wherein the upper grip is connected to the upper portion of the frame, the lower grip is connected to the lower portion of the frame, and the upper interface and the lower interface both define a boundary wherein the test article is engaged with either the upper grip or the lower grip;
   urging the upper grip in an upward direction and towards the upper portion of the panel by an adjustment mechanism of a tensioner assembly, wherein the tensioner assembly is located at the upper portion of the test fixture and is connected to the upper grip;
   pulling an upper adapter plate upwardly as tension is exerted upon the test article, wherein the upper adapter plate connects the tensioner assembly to the upper grip and defines a plurality of elongated apertures that each receive a corresponding upper fastener, wherein the elongated profile of the apertures allow for the upper adapter plate to be pulled upwardly;
   maintaining a lower adapter plate substantially static as tension is exerted upon the test article, wherein the lower adapter plate defines a plurality of substantially round apertures for each receiving a corresponding lower fastener;
   transporting a cooling medium across at least one of the upper interface and the lower interface by a cooling assembly; and
   directing the cooling medium across one of the upper interface and the lower interface by an inlet manifold, wherein the inlet manifold defines at least one opening, and wherein a pair of front frame members are each positioned at an opposing side of the test fixture and the inlet manifold is secured to one of the front frame members.

18. The method of claim 17, comprising receiving the cooling medium directed across one of the upper interface and the lower interface by an opening defined by an outlet manifold.

19. A test fixture for securing a test article, the test fixture comprising:
   a frame defining an upper portion and a lower portion, wherein the lower portion of the frame is configured to be releasably mounted to a vibration device;
   an upper grip connected to the upper portion of the frame and a lower grip connected to the lower portion of the frame, wherein the upper grip is configured to secure an upper portion of the test article along an upper interface, the lower grip is configured to secure a lower portion of the test article along a lower interface, and the upper interface and the lower interface both define a boundary wherein the test article is engaged with either the upper grip or the lower grip;
   a tensioner assembly located at the upper portion of the test fixture, wherein the tensioner assembly is connected to the upper grip and includes an adjustment mechanism configured to urge the upper grip in an upward direction towards the upper portion of the frame;
   an upper adapter plate connecting the tensioner assembly to the upper grip, wherein the upper adapter plate defines a plurality of elongated apertures that each receive a corresponding upper fastener, and wherein the elongated profile of the apertures allow for the upper adapter plate to be pulled upwardly as tension is exerted upon the test article;

a lower adapter plate defining a plurality of substantially round apertures for each receiving a corresponding lower fastener, wherein the lower adapter plate remains substantially static as tension is exerted upon the test article;

a cooling assembly configured to transport a cooling medium across at least one of the upper interface and the lower interface;

an inlet manifold defining at least one opening to direct the cooling medium across one of the upper interface and the lower interface;

an outlet manifold defining at least one opening in fluid communication with the at least one opening of the inlet manifold; and a pair of front frame members each positioned at an opposing side of the test fixture, wherein the inlet manifold is secured to one of the front frame members and the outlet manifold is secured to a remaining one of the front frame members.

20. A test fixture for securing a test article, the test fixture comprising:

a frame defining an upper portion and a lower portion, wherein the lower portion of the frame is configured to be releasably mounted to a vibration device;

an upper grip connected to the upper portion of the frame and a lower grip connected to the lower portion of the frame, wherein the upper grip is configured to secure an upper portion of the test article along an upper interface, the lower grip is configured to secure a lower portion of the test article along a lower interface, and the upper interface and the lower interface both define a boundary wherein the test article is engaged with either the upper grip or the lower pip;

a tensioner assembly located at the upper portion of the test fixture, wherein the tensioner assembly is connected to the upper grip and includes an adjustment mechanism configured to urge the upper grip in an upward direction towards the upper portion of the frame;

an upper adapter plate connecting the tensioner assembly to the upper grip, wherein the upper adapter plate defines a plurality of elongated apertures that each receive a corresponding upper fastener, and wherein the elongated profile of the apertures allow for the upper adapter plate to be pulled upwardly as tension is exerted upon the test article;

a lower adapter plate defining a plurality of substantially round apertures for each receiving a corresponding lower fastener, wherein the lower adapter plate remains substantially static as tension is exerted upon the test article;

a cooling assembly configured to transport a cooling medium across at least one of the upper interface and the lower interface;

at least one heat shield positioned to insulate at least one of the upper grip and the lower grip; and an insulation blanket and a beam, wherein the beam compresses the insulation blanket to create a substantially fluid-tight seal against the insulation blanket and an outer surface of the test article.

* * * * *